United States Patent
Satyawali et al.

(10) Patent No.: US 11,180,783 B2
(45) Date of Patent: Nov. 23, 2021

(54) METHOD FOR PRODUCING CHIRAL AMINES

(71) Applicant: VITO NV, Mol (BE)

(72) Inventors: Yamini Satyawali, Mol (BE); Dominic Ormerod, Mol (BE); Claudia Matassa, Mol (BE); Karolien Vanbroekhoven, Mol (BE)

(73) Assignee: VITO NV, Mol (BE)

( * ) Notice: Subject to any disclaimer, the term of this patent is extended or adjusted under 35 U.S.C. 154(b) by 0 days.

(21) Appl. No.: 16/643,829

(22) PCT Filed: Aug. 31, 2018

(86) PCT No.: PCT/EP2018/073524
§ 371 (c)(1),
(2) Date: Mar. 2, 2020

(87) PCT Pub. No.: WO2019/043186
PCT Pub. Date: Mar. 7, 2019

(65) Prior Publication Data
US 2021/0062233 A1    Mar. 4, 2021

(30) Foreign Application Priority Data

Sep. 1, 2017 (EP) .................... 17188951

(51) Int. Cl.
*C12P 13/00* (2006.01)
*C12N 9/10* (2006.01)

(52) U.S. Cl.
CPC .......... *C12P 13/001* (2013.01); *C12N 9/1096* (2013.01)

(58) Field of Classification Search
CPC ............................. C12P 13/00; C12N 9/1096
See application file for complete search history.

(56) References Cited

U.S. PATENT DOCUMENTS 10,017,749 B2 * 7/2018 Hanlon ................ C12P 13/001
10,730,022 B2 * 8/2020 Satyawali ............ C12P 13/001

FOREIGN PATENT DOCUMENTS

WO    201008153 A2    7/2010
WO    2017103163 A1   6/2017

OTHER PUBLICATIONS

Ceriolo, et al.; "Characterization of a novel amine transaminase from Halomonas elongata", Journal of Molecular Catalysis B: Enzymatic, vol. 120, Jul. 21, 2015.
Ehimen et al.; "Application of membrane contactor as a process intensification approach for chiral amine sythesis" 10th European Congress of Chemical Engineering, http://www.ecce2015.eu/index.php/program/synopsis-program, 2015.
Gao et al.; "Characterization of a (R)-selective amine transaminase from Fusarium oxysporum"; Process Biochemistry, Aug. 30, 2017.
Gomm et al.; "A new generation of smart amine donors for transaminase-mediated biotransformations", Chemistry—A European Journal, vol. 22, Aug. 3, 2016.
Green et al.; "Chiral amine synthesis using omega-transaminases: An amine donor that displaces equilibria and enables high-throughput screening", Angewandte Chemie—International Edition, vol. 53, Aug. 19, 2014.
Gundersen et al.; "Amine donor and acceptor influence on the thermodynamics of omega-transaminase reactions", Tetrahedron: Asymmetry, vol. 26, Apr. 23, 2015.
Patil et al.; "Recent advances in omega-transaminase-mediated biocatalysis for the enantioselective synthesis of chiral amines", Catalysts, vol. 8, Jun. 21, 2018.
Satyawali et al.; "Asymmetric synthesis of chiral amine in organic solvent and in-situ product recovery for process intensification: A case study", Biochemical Engineering Journal, vol. 117, Nov. 9, 2016.
European Patent Office, International Search Report and Written Opinion of the International Search Authority of the International Searching Authority, dated Oct. 19, 2018 in PCT/EP2018/073524, which is the international application to this U.S. application.

* cited by examiner

*Primary Examiner* — Tekchand Saidha
(74) *Attorney, Agent, or Firm* — Kolitch Romano LLP

(57) ABSTRACT

A method for producing a chiral amine may include performing a transamination reaction of a prochiral amino acceptor and an amino donor in a first solution in the presence of a transaminase, thereby forming a chiral amine and a co-product in the first solution. The amino donor is a high molecular weight (HMW) amino donor. In some examples, the molecular weight of the HMW amino donor is at least 150 g/mol. In some examples, the amino donor is affixed on a support, the total molecular weight of the amino donor and the support being at least 150 g/mol.

20 Claims, 15 Drawing Sheets

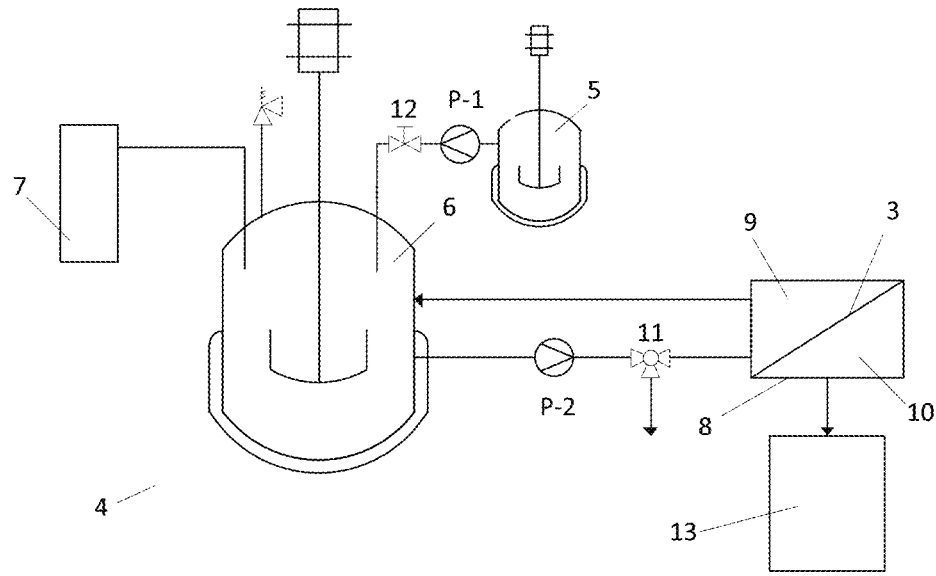
Fig. 3
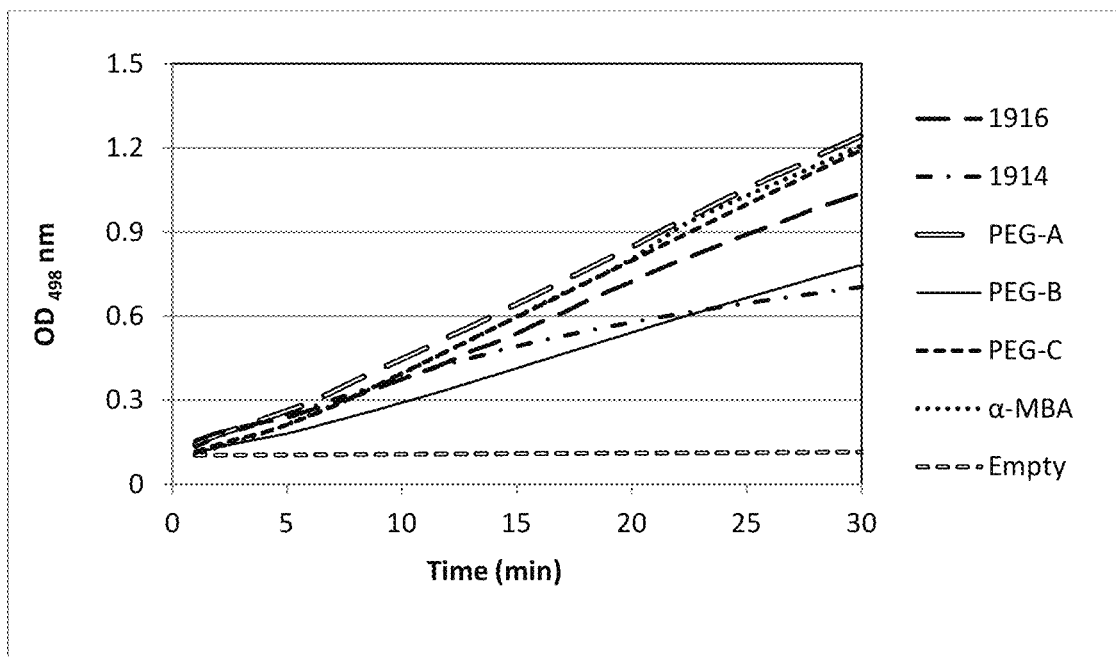
Fig. 4.1

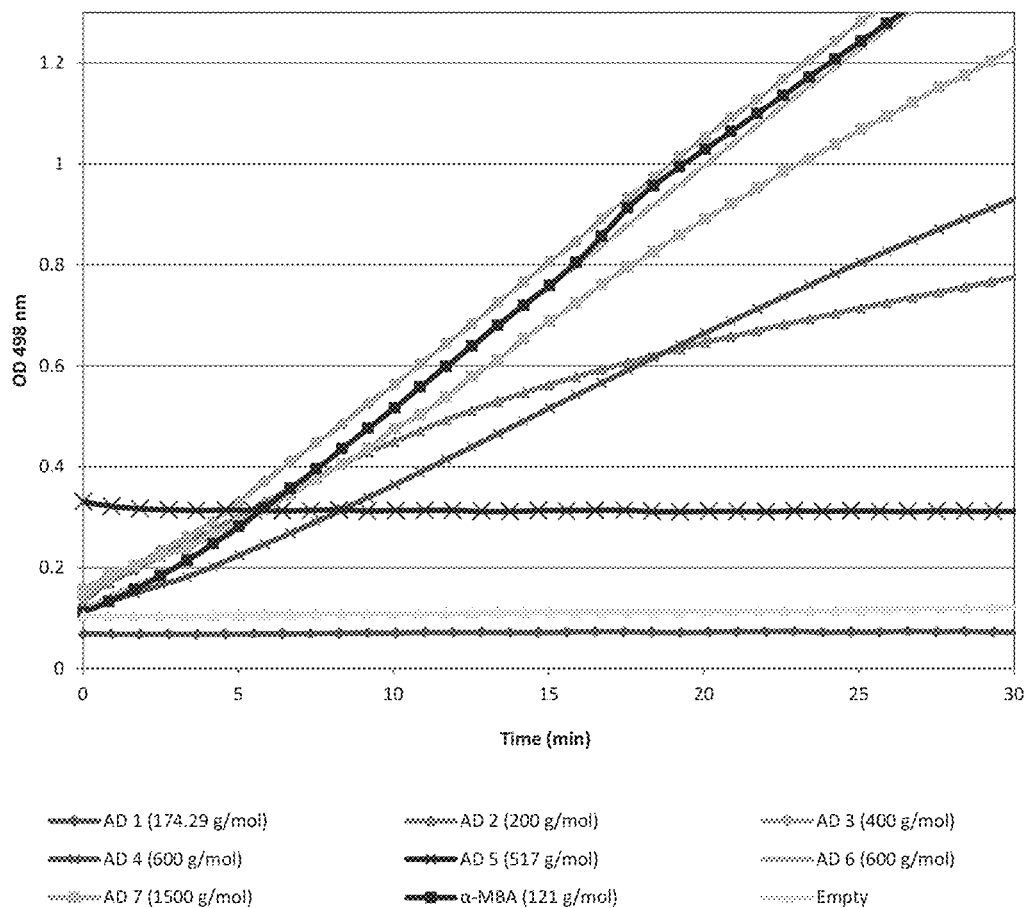
Fig. 4.2
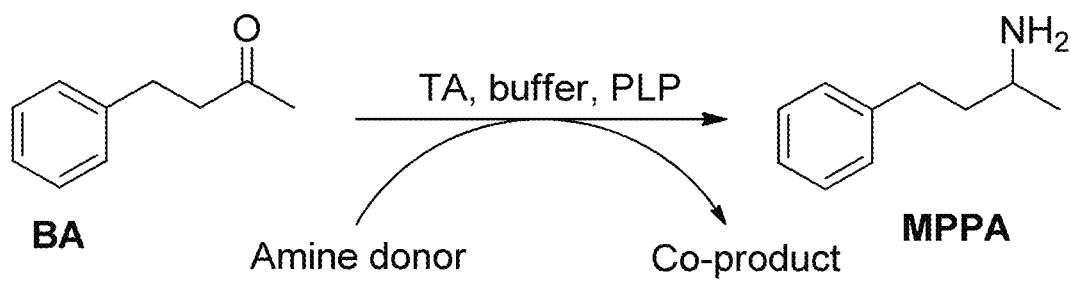
Fig. 4.3

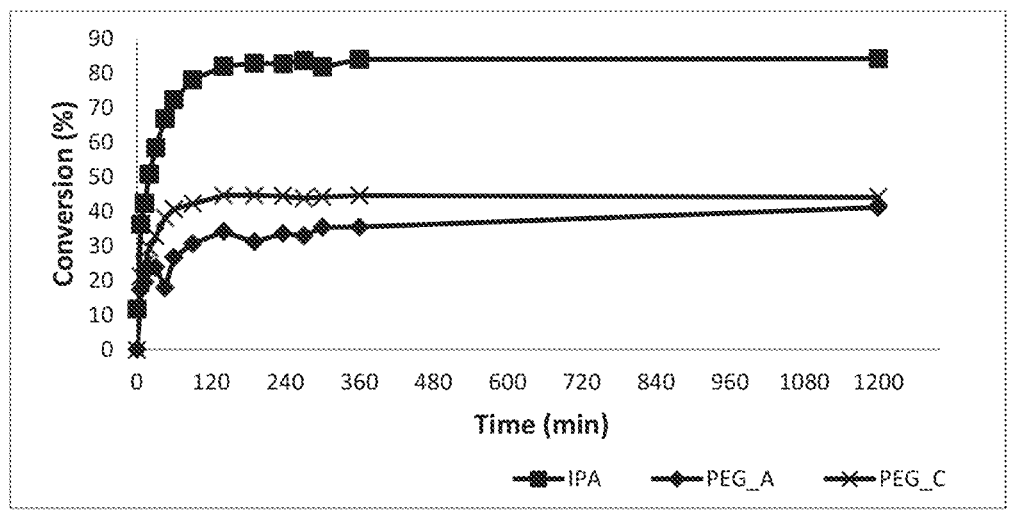
Fig. 5.1
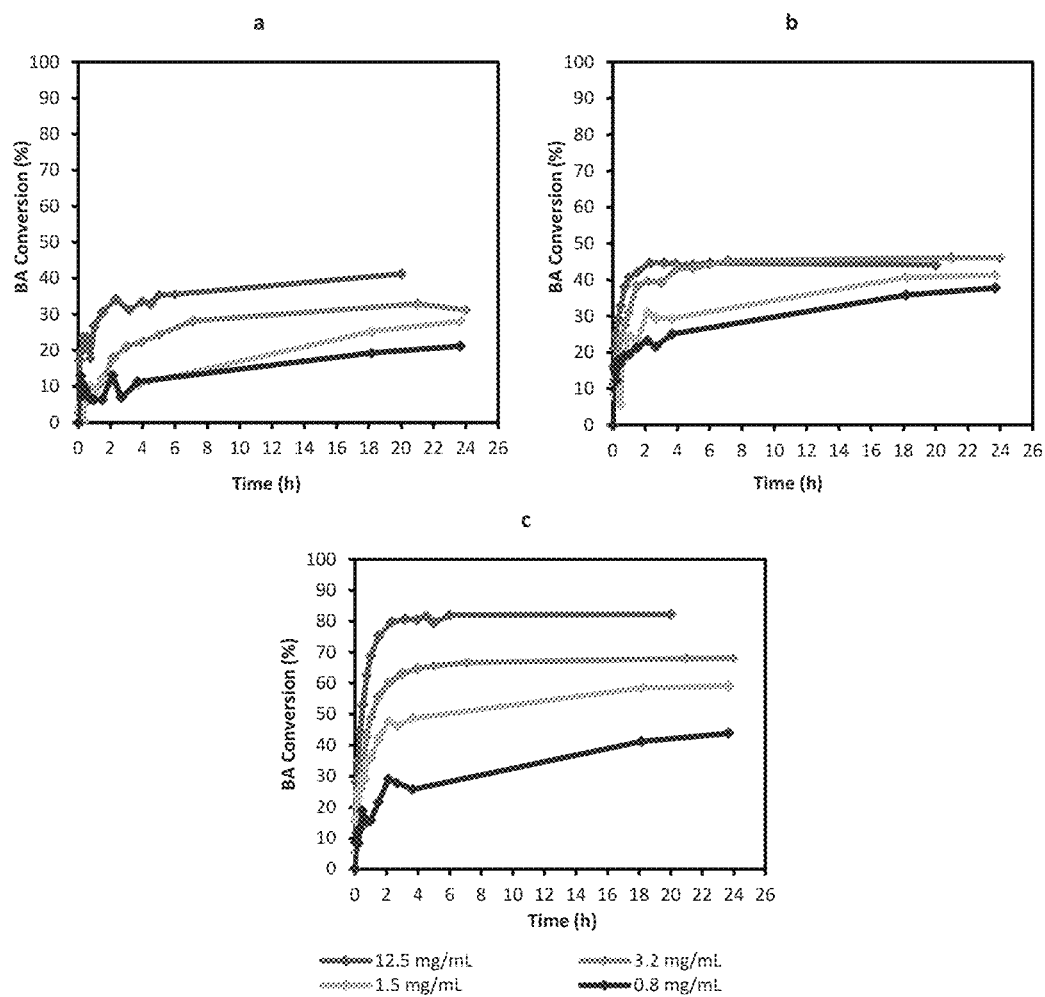
Fig. 5.2

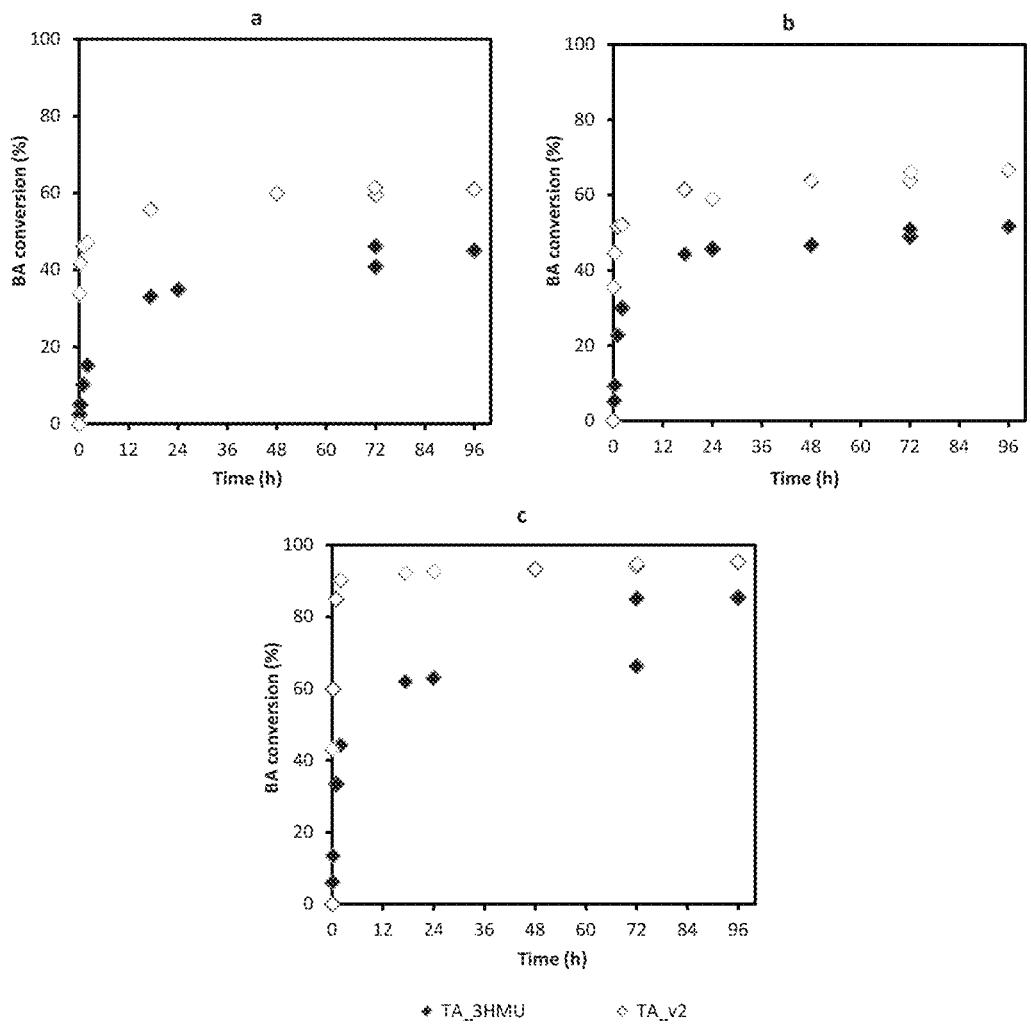
Fig. 5.3

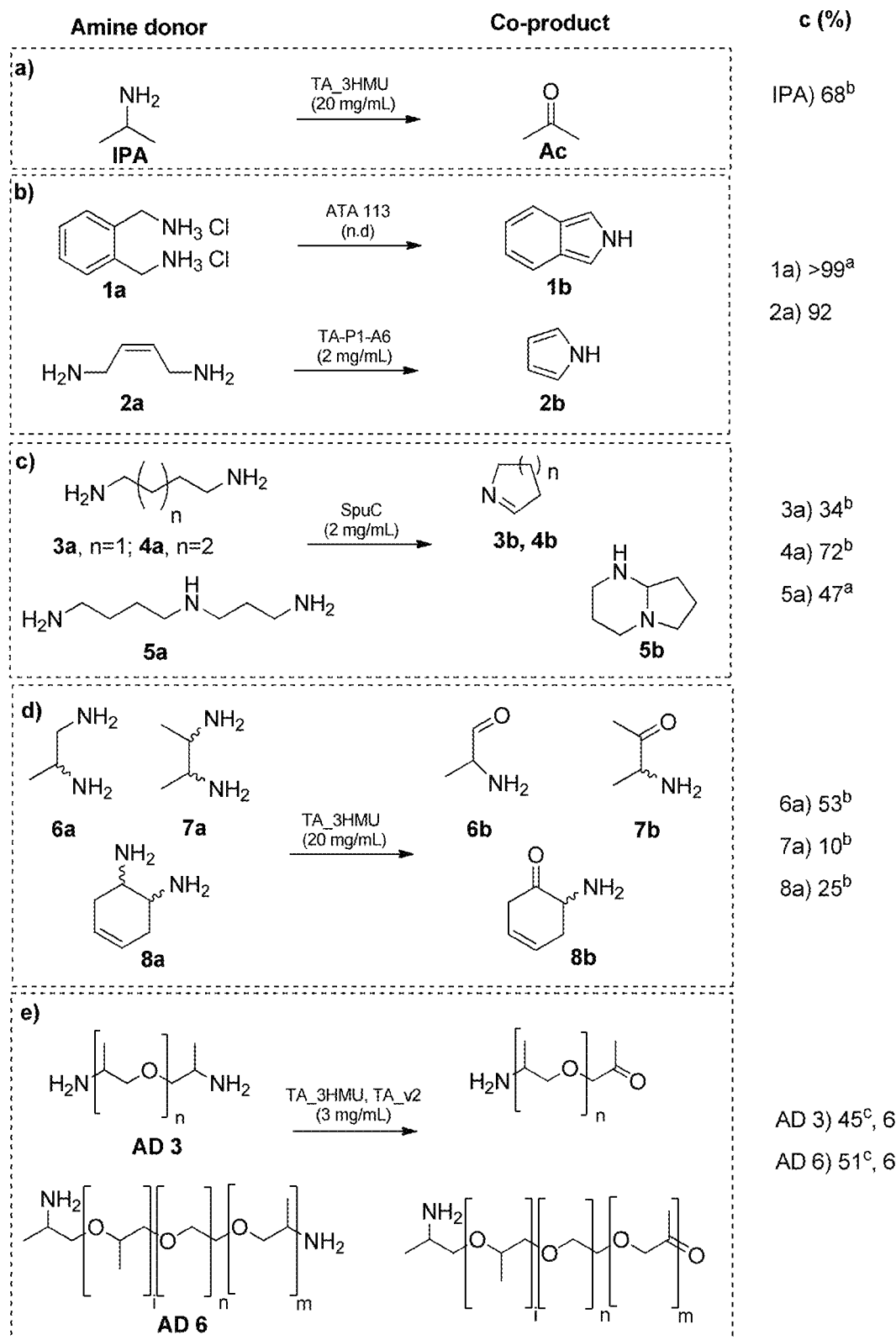
Fig. 5.4

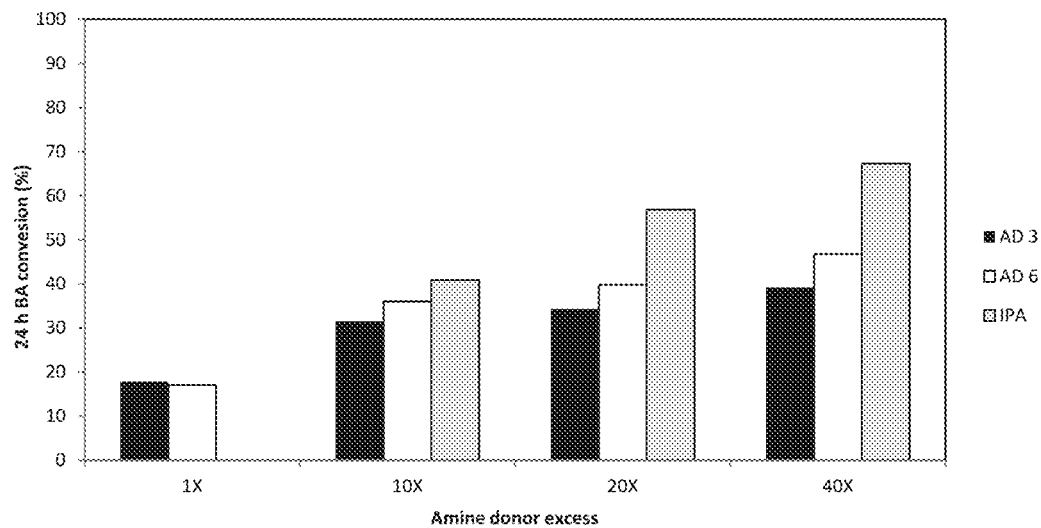
Fig. 9.2
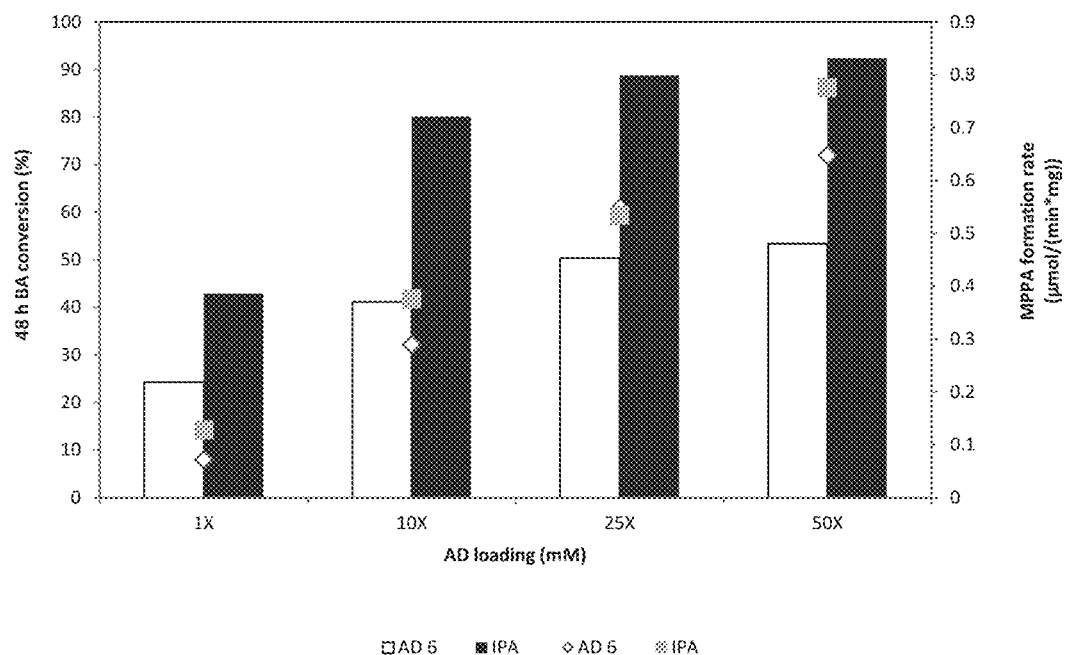
Fig. 9.3

METHOD FOR PRODUCING CHIRAL AMINES

TECHNICAL FIELD

The present disclosure is related to methods for producing amines, more particularly chiral amines using transaminase biocatalysts.

INTRODUCTION

Amines and, particularly chiral amines, are key building blocks in many pharmaceutical, agrochemical and chemical applications. Chiral amines are of great importance in the preparation of various physiologically, for instance pharmaceutically, active substances. In many of the applications only one particular optically active form of the chiral amines, either the (R) or the (S) enantiomer, has the desired physiological activity.

(Chiral) amines can be produced both by chemical and biocatalytic synthesis routes. Chemical methods for synthesis of optically active chiral amine are often multi-step processes with challenging purification operations. Chemical synthesis of chiral amines via a one-step procedure, on the other hand, requires high chemo-, regio-, diastereo- and enantiocontrol.

During the last decade, a biocatalytic synthesis route using the enzyme transaminases (EC 2.6.1.X; also known as aminotransferases) has been identified as a very powerful method for chiral amine synthesis compared to the chemical methods known in the art. Transaminases (TAs) are pyridoxal phosphate (PLP) dependent enzymes and catalyze the transfer of an amino group ($-NH_2$) from an amino donor, for instance an amine such as 2-propylamine, to a pro-chiral amino acceptor, yielding a (chiral) amine as well as a co-product, in the presence of the cofactor pyridoxal phosphate which is continuously regenerated during the reaction. The transaminase (TA) catalyzed transamination reaction is schematically represented in FIG. 1. Transaminases, particularly (R)- and (S)-selective transaminases, have thus received much attention as suitable catalysts for producing chiral amines, as they allow the direct asymmetric synthesis of (optically active) chiral amines from pro-chiral amino acceptors. Indeed, in case $R_1$ and $R_2$ are different (and not being $-NH_2$), the produced amine (amine product) represented in FIG. 1 is a chiral amine.

Although the transaminase catalyzed synthesis of chiral amines presents a high enantio- and regioselectivity, the transamination reaction is a reversible reaction, often with an unfavorable thermodynamic equilibrium which favors the substrate side (i.e. left side from the reaction arrow in FIG. 1) more than the amine product side (i.e. right side from the reaction arrow in FIG. 1) and hence limits obtaining high chiral amine yields. Accordingly, an amine mixture is obtained comprising the chiral amine product and the amino donor, requiring further purification of the chiral amine. However, as in general in a transamination process the amino donor and the formed amine have very similar properties (due to their similar main functional groups), it is often difficult to further separate them. In addition, the transaminase catalyzed chiral amine synthesis is prone to substrate and product inhibition. Substrate solubility issues may hinder the reaction as well.

In the art, several ways have already been proposed to deal with the above mentioned drawbacks of the transamination reaction.

In almost all the transamination reactions reported so far, for instance, the amino donor is provided in excess so as to shift the thermodynamic equilibrium of the reaction to the amine product side. More particularly, the excess amino donor is provided in ranges from 5 to 100 times (or even more) compared to the ketosubstrate. However, after the completion of the reaction, the excess (unreacted) amino donor is wasted, which involves a high donor substrate cost. In literature, also other physical and chemical strategies have been described (as for instance summarized by Guo et al. in Green Chem., 2017, 19, 333-360). For example, next to providing the amino donor in excess, the equilibrium can be shifted to the amine product side of the reaction by removal of the formed amine product, co-products, and/or by performing biochemical cascade reactions.

Other chiral amine synthesis routes already developed in the art perform separations of substrates and products based on different pKa and hydrophobicity between substrates and products, as for instance described by Rehn et al. in J. Biotechnol., 2014, 179, 50-55 and Rehn et al. in J. Mol. Catal. B: Enzym., 2016, 123, 1-7.

Borner et al. in Org. Process Res. Dev., 2015, 19(7), 793-799, for example, describes an enzymatic chiral amine synthesis process setup combined with a selective solvent extraction of the product chiral amine, comprising a so-called reaction phase and a so-called stripping phase at different pH, separated by a supported liquid membrane. More particularly, alanine is investigated as an amino donor for the reductive amination of a poorly water-soluble ketone (4-phenyl-2-butanone) in a combined in situ product removal (ISPR) approach using liquid-membrane extraction together with an enzyme cascade. The ISPR strategy facilitates very high (more than 98%) product purity with an integrated enrichment step (without any additional purification step), and eliminates product as well as co-product inhibition. For reactions using isopropyl amine (IPA) as an amino donor, however, the product solution is contaminated with the IPA passing through the membrane, leading again to a loss of donor substrate and low product purity. Hence, despite its often more favorable reaction equilibrium, IPA reactions require further downstream operations to yield similar purity as achieved with ALA. In this way, the production route for obtaining a sufficient amount of the desired chiral amines remains complex, negatively affecting the economics of recovery of the formed amine product. Moreover, the liquid-membrane setup used in this study is not stable due to the liquid in the membrane pores being prone to leaking out during operation, requiring regularly regeneration of the liquid membrane. Additionally, the liquid-membrane setup is sensitive to transmembrane pressure differences. Hence, the setup is less suitable for long-term, large (industrial) scale chiral amine synthesis and separation.

A process for producing high yields of enantioselective amino acids and chiral amines is for example described in US 2009/0298134, reacting a keto acid or ketone and an amino acid donor in the presence of a transaminase biocatalyst to produce a keto acid by-product and an amino acid or amine product. Further reacting the keto acid by-product with a peroxide increases the yield of additional amino acid or amine product. However, this renders the production of chiral amines complex, involving a relatively high processing cost.

SUMMARY

Despite efforts already made in the art, there is a need for providing improved methods for producing amines, more particularly chiral amines, using transaminase biocatalysts shifting the thermodynamic equilibrium to the amine product side, thereby avoiding amino donor loss. It is an aim of the present disclosure to provide such methods, at the same time allowing for a long term, scalable application.

It is additionally an aim of the present disclosure to provide simplified methods for producing chiral amines with high yield and high product purity, the methods being more efficient and cost effective (compared to prior art methods).

According to an aspect of the present disclosure, there is therefore provided a method for producing (optically active) chiral amines as set out in the appended claims. The method comprises the step of performing a transamination reaction of a prochiral amino acceptor and an amino donor in a first solution (or reaction solution) in the presence of a transaminase, thereby forming a chiral amine product and a co-product in said first solution. The molecular weight (MW) of the amino donor is at least 150 g/mol (advantageously at least 200 g/mol, advantageously at least 300 g/mol) (referred to as high molecular weight (HMW) amino donor). Alternatively, the amino donor is affixed on (linked to, immobilized on) a (chemically inert) support, the total molecular weight of the amino donor and the support being at least 150 g/mol (advantageously at least 200 g/mol, advantageously at least 300 g/mol). The high molecular weight of the amino donor (or of the amino donor together with the support) advantageously provides an improvement of the downstream processing after having performed the transamination reaction. More particularly, due to the HMW of the amino donor (or of the amino donor together with the support) only a limited downstream processing, or advantageously even no further downstream processing, is to be performed after having performed the transamination reaction, for recovery of the amine product with high yield and high product purity. Hence, the recovery and purification of the formed amine product can be improved compared to the known methods in the art. Advantageously, the donor amine is provided in excess thereby shifting the thermodynamic equilibrium to the amine product side of the transaminase catalyzed reaction.

Further advantageous aspects of the present disclosure are set out in the dependent claims. The chiral amine production method is thereby combining the transaminase catalyzed reaction between a donor amine and prochiral amino acceptor in a first solution (or reaction solution) with a porous membrane based separation of the produced chiral amine. Advantageously, the membrane is selected based on its MWCO (and/or pore size) so as to only enable the formed amine product to pass through the membrane. The produced chiral amine is thereby selectively removed across the membrane from the first solution thereby forming a second solution (advantageously permeate, or permeate solution), while at the same time, based on their (high) molecular weight, donor amine provided in excess, transaminase, and formed co-product are retained in the reaction solution. The chiral amine can hence be formed with high product purity. Methods of aspects of the disclosure thus allow for shifting the thermodynamic equilibrium to the amine product side of the transaminase catalyzed reaction, thereby reducing and even avoiding loss of the amino donor provided in excess. The amino donor provided in excess thereby remains available for further transaminase reaction. In this way, the amount of excess amino donor, needed to shift the thermodynamic equilibrium of the reaction to the amine product side, can be reduced compared to prior art methods, thereby lowering the substrate cost. Indeed in prior art, to the contrary, excess amino donor is wasted during/after the transamination reaction and hence has to be provided regularly to keep the transaminase reaction ongoing, involving a high donor substrate cost.

According to another aspect of the present disclosure, there is provided a chiral amine production and separation unit (or device) (4) comprising:

- a first vessel (5) for holding an amino donor and a prochiral amino acceptor, the first vessel (5) being in fluid connection with an enzyme tank (6) for holding a first solution (1) comprising a transaminase, and a means for providing amino donor and prochiral amino acceptor from the first vessel (5) to the enzyme tank (6) thereby forming a chiral amine and a co-product in the first solution (1) in tank (6), advantageously a valve (12) is arranged between the first vessel (5) and the enzyme tank (6);
- optionally a second vessel (7) for holding an inert gas being in fluid connection with the enzyme tank (6) and a means for providing a flow of inert gas to the enzyme tank (6);
- a membrane unit (8) arranged downstream from the enzyme tank (6), said membrane unit (8) being in fluid connection with the enzyme tank (6), and said membrane unit (8) comprising a first compartment (9) separated by a porous membrane (3) from a second compartment (10), advantageously a (three-way) valve (11) is arranged between the enzyme tank (6) and the (first compartment (9) of the) membrane unit (8);
- the first compartment (9) of the membrane unit (8) is configured for receiving the first solution (1) (comprising formed chiral amine) from the enzyme tank (6), the second compartment (10) is configured for holding a second solution (2), advantageously the second solution (2) is the permeate (or filtrate) of the first solution (said permeate formed by permeating the chiral amine product from the first solution (1) across the porous membrane (3));
- a third vessel (13) for recovering (collecting) the second solution (2) (advantageously permeate solution) comprising the formed amine, said third vessel (13) being arranged downstream from the membrane unit (8), said third vessel (13) being in fluid connection with the second compartment (10) of the membrane unit (8), advantageously a means for controlling the flow rate of the second solution (2) (for example a valve) is arranged between the (second compartment (10) of the) membrane unit (8) and the third vessel (13);
- optionally a means for recirculating the first solution (1) (advantageously comprising excess donor amine) from the first compartment (9) of the membrane unit (8) back into the enzyme tank (6).

Advantageously, the porous membrane is a nanofiltration (NF) membrane, advantageously, a polymeric or ceramic nanofiltration membrane.

Advantageously, the porous membrane has a MWCO for amino donor and transaminase of at least 150 g/mol (advantageously of at least 200 g/mol, advantageously of at least 300 g/mol), and/or the pore size of the pores of the porous membrane ranges from 0.5 nm to 100 nm (advantageously from 0.5 nm to 50 nm, advantageously from 0.5 nm to 20 nm, advantageously from 1 nm to 10 nm).

Advantageously, the chiral amine production and separation unit (4) comprises a means for applying a pressure across the porous membrane (3).

BRIEF DESCRIPTION OF THE DRAWINGS

Aspects of the present disclosure will now be described in more detail with reference to the appended drawings, wherein same reference numerals illustrate same features and wherein:

FIG. 3 schematically represents a chiral amine production and separation unit (4);

FIG. 4.1 shows the increase of absorbance at 498 nm at 37° C. over time for transaminase 3HMU when using different amino donors (right side of FIG. 4.1) and experimental slopes obtained (left side of FIG. 4.1);

FIG. 4.2 shows the increase of absorbance at 498 nm at 37° C. over time for transaminase 3HMU when using different amino donors (right side of FIG. 4.2) and experimental slopes obtained (left side of FIG. 4.2). In FIG. 4.2 the result for AD 5 is also included, compared to FIG. 4.1;

FIG. 4.3 schematically represents a model transamination reaction, with BA as amino acceptor and PEG-C (or AD 6, cf. Table 1) being employed as amine donor.

FIG. 9.2 shows 24 h conversion of substrate (BA) when using different amine donor loadings. 3.125 mg/mL crude extract lyophilized TA_3HMU was used;

FIG. 9.3 shows 48 h conversion of BA substrate (left axis) and MPPA formation rate (right axis) when using different amine donor loadings. 0.5 mg/mL heat purified TA_v2 was used;

DETAILED DESCRIPTION

Figure 1:
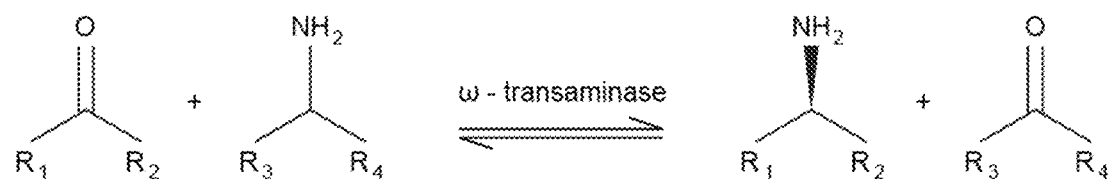
FIG. 1 schematically represents the transaminase catalyzed transamination reaction, whereby an amino acceptor (a substrate ketone) and an amino donor (a substrate amine) are transformed into an amine product and a co-product (ketone). In case $R_1$ and $R_2$ are different (and not an amino group —$NH_2$), the amine product is a chiral amine.

Methods for producing a (optically active) chiral amine according to aspects of the present disclosure include a step of performing a transamination reaction of a prochiral amino acceptor and an amino donor in a first solution (1) (or reaction solution) in the presence of a transaminase, thereby forming a chiral amine product and a co-product (ketone) in said first solution. The transamination reaction (in the reaction solution) is schematically represented in FIG. 1. In aspects of the present invention, the amino donor is a high molecular weight (HMW) amino donor, the molecular weight of the high molecular weight amino donor being at least 150 g/mol (advantageously at least 200 g/mol, advantageously at least 300 g/mol); or said amino donor is affixed on (linked to, immobilized on) a (inert) support, the total molecular weight of the amino donor and the support being at least 150 g/mol (advantageously at least 200 g/mol, advantageously at least 300 g/mol).

Advantageously, the amino donor is a HMW amino donor, the molecular weight of the HMW amino donor being at least 150 g/mol (advantageously at least 200 g/mol, advantageously at least 300 g/mol).

Alternatively, in case the amino donor is affixed on a support, the amino donor is a low molecular weight (LMW) amino donor affixed on (linked to, immobilized on) a (inert) support, the total molecular weight of the amino donor and the support being at least 150 g/mol (advantageously at least 200 g/mol, advantageously at least 300 g/mol). The molecular weight of the LMW amino donor is below 150 g/mol. Advantageously, the LMW amino donor is selected from the group consisting of isopropylamine, glycine, alanine, butylamine, and lysine.

More advantageously, the molecular weight of the HMW amino donor, or the total molecular weight of the (LMW) amino donor and the support, is at least 180 g/mol, advantageously at least 200 g/mol, advantageously at least 300 g/mol.

Advantageously, the support (or carrier) is an inert support, i.e. not actively participating in the transamination reaction. Advantageously the support is a polystyrene support, advantageously a polystyrene support comprising chlorine (such as cross-linked polystyrene resins carrying a chloromethyl functional group (or surface chloromethylated polystyrene beads), e.g. commercially available as Merrifield's peptide resins by Sigma-Aldrich®).

In the context of the present description, total molecular weight of the (LMW) amino donor and the support refers to the sum of the molecular weight of the (LMW) amino donor and the molecular weight of the support.

Methods of the present disclosure use a high molecular weight (HMW) amino donor (or a (LMW) amino donor linked to a support, the total structure together having a high molecular weight), whereas transamination reactions described in the art up to now always use low molecular weight amino donors having a molecular weight below 150 g/mol. Börner et al. in Org. Process Res. Dev., 2015, 19(7), 793-799, for example, use alanine and isopropylamine as amino donor in the transamination reaction having a molecular weight of about 89 g·mol$^{-1}$ and 59 g·mol$^{-1}$, respectively. The skilled person in the art in fact does not expect that using amino donors with higher molecular weight would react in a transamination reaction (which is known to be stereospecific) due to the higher steric hindrance the larger size of substituent groups of the HMW amino donor will involve. Hence, large (or HMW) amino donors have never been employed for biocatalytic transamination reactions so far. In fact, larger amino donors are quite challenging for transamination reactions.

With the present application, it has surprisingly been observed that methods using a high molecular weight (HMW) amino donor (or a (LMW) amino donor linked to a support, the total structure together having a high molecular weight) do successfully react in a transamination reaction. Moreover, it has been observed that using such HMW amino donor (or a (LMW) amino donor linked to a support, the total structure together having a high molecular weight) allow for an improved downstream processing (i.e. a limited downstream processing or even no further downstream processing to be performed) after having performed the transamination reaction (compared to prior art methods). More particularly, the methods of aspects of the present disclosure are more efficient, allowing to increase the volumetric productivity of the formed amine product without losing the excess of amino donor necessary for shifting the equilibrium to the amine product side. The amine product is thereby formed with high yield and high product purity.

In the context of the present description, an "amino acceptor" refers to a carbonyl compound which accepts an amino group from an amino donor or donor amine. Advantageously, the amino acceptor contains a ketone (or keto) functionality and is also referred to as "acceptor ketone", "ketone substrate", "ketosubstrate", or "substrate ketone". The selection of the acceptor ketone typically depends on the desired chiral amine.

In the context of the present description, "amino donor", "donor amine", "amine donor", "amine substrate", "amino substrate", or "substrate amine" refers to any molecule that will react with a transaminase and an acceptor ketone by providing an amino group ($NH_2$) to the acceptor ketone.

In aspects of the present disclosure, advantageously, the HMW amino donor is an amine or an amino acid, advantageously, the HMW amino donor is an amine. The amino donor advantageously comprises at least one amino group (i.e. one, two, three, or more amino groups). The amino donor can thus comprise one amino group or more than one amino groups. At least one amino group is hence available for transamination. Advantageously, the amino donor comprises at least one primary amino group. More advantageously, the amino donor comprises two (primary) amino groups. In such case, one amino group can be used in the transamination reaction while the other amino group can link to another amino donor to form yet a larger amino donor. In this way, the excess amount of amino donor, needed to shift the thermodynamic equilibrium of the reaction to the amine product side, can be (further) reduced, hence (further) lowering the substrate costs (compared to prior art methods).

More advantageously, the HMW amino donor is an amine having the general formula:

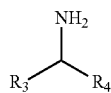

wherein the substituents $R_3$ and $R_4$ are the same or different from each other (the hydrogen bonded to the carbon not being depicted in the above general formula); and wherein each of $R_3$ and $R_4$ is independently selected from the group consisting of: hydrogen; linear or branched saturated alkyl group; linear or branched unsaturated alkyl group; cycloalkyl group; heterocyclyl group; heterocyclylalkyl group; aryl group; aralkyl group; heteroaryl group; acyl group; hydroxyl group; linear or branched saturated alcohol; linear or branched unsaturated alcohol; alkoxy group; aryloxy group; amino group; alkylamino group; cycloalkylamino group; arylamino group; acyloxy group; acylamino group; cyano group; nitrile; carboxyl group; thio group; thiol group; aminocarbonyl group; carbamoyl group; arlyoxycarbonyl group; phenoxycarbonyl group; alkoxycarbonyl group; haloalkyl group; and halogen.

For example, commercially available JEFFAMINE® polyetheramines provided by Huntsman can be used as HMW amino donors. The JEFFAMINE® polyetheramines are highly versatile and cheap, containing primary amino groups attached to the end of a polyether backbone.

Advantageously, the HMW amino donor is selected from the group consisting of (highly flexible) poly(ethylene glycol) bis (3-aminopropyl);

1,4-bis(3-aminopropyl)piperazine;

poly(propylene glycol) bis(2-aminopropyl ether) (i.e. PEG-A, JEFFAMINE® provided by Huntsman);

O-(2-aminopropyl)-O'-(2-methoxyethyl)polypropylene glycol (i.e. PEG-B);

O,O'-bis(2-aminopropyl) polypropylene glycol-block-polyethylene glycol-block-polypropylene glycol (i.e. PEG-C, JEFFAMINE® provided by Huntsman); and 1,2-bis(3-aminopropylamino)ethane.

In aspects of the present disclosure, advantageously, the prochiral amino acceptor is a ketone substrate. More advantageously, the prochiral amino acceptor is a ketone substrate having the general formula:

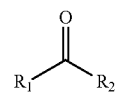

wherein the substituents $R_1$ and $R_2$ are different from each other (and each of $R_1$ and $R_2$ not being an amino group $-NH_2$); and wherein each of $R_1$ and $R_2$ is independently selected from the group consisting of: hydrogen; linear or branched saturated alkyl group; linear or branched unsaturated alkyl group; cycloalkyl group; heterocyclyl group; heterocyclylalkyl group; aryl group; aralkyl group; heteroaryl group; acyl group; hydroxyl group; linear or branched saturated alcohol; linear or branched unsaturated alcohol; alkoxy group; aryloxy group; amino group; alkylamino group; cycloalkylamino group; arylamino group; acyloxy group; acylamino group; cyano group; nitrile; carboxyl group; thio group; thiol group; aminocarbonyl group; carbamoyl group; arlyoxycarbonyl group; phenoxycarbonyl group; alkoxycarbonyl group; haloalkyl group; and halogen.

More advantageously, the amino acceptor is a ketone substrate selected from the group consisting of acetophenone (molecular weight of about 120 g/mol), ortho-bromoacetophenone (molecular weight of about 199 g/mol), benzylacetone (molecular weight of about 148 g/mol), and 2-bromo-4-acetylacetanilide (molecular weight of about 256 g/mol).

Acetophenone can also be referred to as 1-phenylethan-1-one, methyl phenyl ketone, or phenylethanone. Ortho-bromoacetophenone can also be referred to as 2'-bromoacetophenone. Benzylacetone can also be referred to as 4-phenyl-2-butanone, methyl (2-phenyl)-ethyl ketone, 1-phenyl-3-butanone.

In aspects of the present disclosure, advantageously, the method further comprises the step of:
separating the chiral amine from the first solution (1) using a porous membrane (3) (i.e. by membrane separation).

Advantageously, the step of membrane separation is performed by membrane contactors (or liquid-liquid (membrane) extraction), or by membrane filtration (or permeation).

More advantageously, the step of membrane separation is performed by membrane filtration (permeation), thereby applying a pressure across said membrane (3) so as to force the first solution (1) to pass through the membrane (3), the chiral amine product thereby permeating from the first solution (1) across the membrane (3) forming a second solution (2) or permeate solution (or filtrate). Advantageously, a pressure of 5 bar or higher is applied, advantageously between 5 to 30 bar, advantageously between 10 to 30 bar.

As advantageously the HMW amino donor is provided in excess (compared to the provided amount of amino acceptor), the thermodynamic equilibrium is shifted to the amine product side of the transamination reaction. Moreover, in advantageous aspects of the invention, only the amine product will pass through the membrane (3) forming the second solution (2) (advantageously permeate solution), whereas the (excess) HMW amino donor will be retained by the membrane due to its HMW (or its large size), advantageously without any loss of amino donor into the second solution (2). Moreover, because the excess of amino donor is retained by the membrane, the excess can be used again with newly supplied amino acceptor, thereby continuously shifting the thermodynamic equilibrium to the amine product side of the transamination reaction while only the amine product is filtered forming the second solution (2). The amount of excess amino donor can thereby be reduced, lowering the substrate cost, compared to prior art methods (where the excess amino donor is wasted during/after the transamination reaction and hence has to be provided regularly to keep the transaminase reaction ongoing). In this way, the present disclosure provides a very efficient and cost effective method for the production and separation of (chiral) amine products based on size exclusion. Such a separation based on size exclusion following a transamination reaction has never been performed in the art, as HMW amino donors have never been employed for biocatalytic transamination reactions so far.

Figure 2:
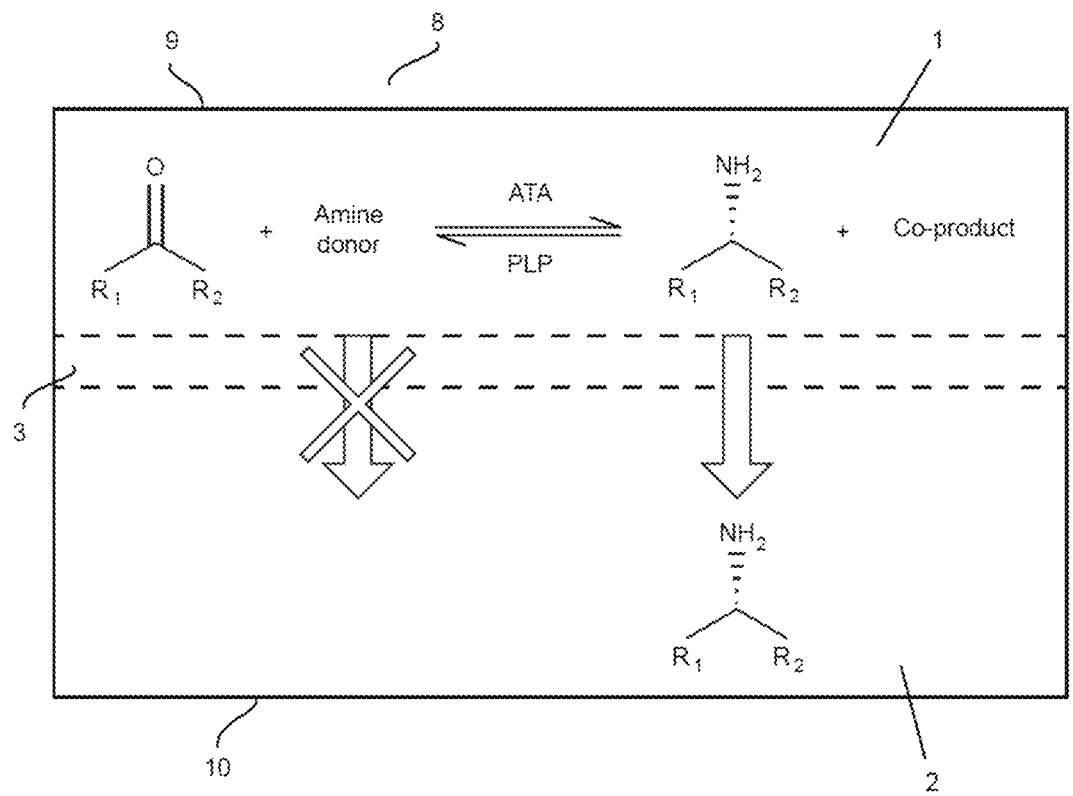
FIG. 2 schematically represents a membrane unit (8) of advantageous aspects of the present disclosure, wherein a porous membrane (3) separates a first compartment (9) containing a first solution (1) and a second compartment (10) containing a second solution (2). The first solution (1) is the reaction solution of the transamination reaction between amino donor and prochiral amino acceptor (ketone substrate) in the presence of, for example, (S)-stereospecific amine transaminases (S-ATA), thereby forming a chiral amine and a co-product. The second solution (2) advantageously is the permeate solution formed by permeating the amine product across the porous membrane (3). Any excess amine donor is rejected by the membrane (3)

Referring to an embodiment of aspects of the disclosure as shown in FIG. 2, a porous membrane (3) separates a first solution (1) (contained in a first compartment (9)) and a second solution (2) (contained in a second compartment (10)). The first solution (1) is the reaction solution of the transamination reaction between amino donor and prochiral amino acceptor (ketone substrate) in the presence of a transaminase thereby forming a chiral amine product and a co-product. The transaminase can for example be a (S)-stereospecific amine transaminase (S-ATA), an important biocatalyst for the production of (S)-amine compounds in a strict stereospecific manner. The second solution (2) advantageously is the permeate solution formed by permeating the amine product from the transaminase reaction across the porous membrane (3). Excess amine donor is rejected by the membrane (3). The first and second compartments (9,10) containing the first and second solutions (1,2), respectively, are comprised in a so-called membrane unit (8) for use in advantageous aspects of the disclosure.

The first solution (1) can be an aqueous solution, advantageously an aqueous alkaline solution; or an organic solvent solution.

Advantageously, an aqueous buffer can be used, such as phosphate buffer, TRIS (tris(hydroxymethyl)aminomethane), EPPS (3-The second solution (2) can be an aqueous solution, or the second solution (2) can be an organic solvent solution (provided that the first solution (1) is a solvent).

Advantageously, the porous membrane has a molecular weight cut-off (MWCO) for each of the amino donor, the transaminase, and the co-product of at least 150 g/mol (advantageously of at least 200 g/mol, advantageously of at least 300 g/mol).

In the context of the present description, molecular weight cut-off (MWCO) refers to the lowest molecular weight in which 80% of the solute is retained by the membrane (or the molecular weight of the molecule that is 80% retained by the membrane).

In advantageous aspects of the present disclosure, the selection of the membrane (for use in a membrane unit (8)) thus depends on the (molecular weight of the) starting substrates and hence on the desired chiral amine product to be formed and recovered.

In advantageous aspects of the disclosure, the membrane is selected based on its MWCO so as to result in a rejection of at least 60%, advantageously of at least 80%, advantageously of at least 90%, advantageously of at least 95% for each of the amino donor, the transaminase, and the formed co-product. The MWCO of the membrane is also selected such that using the membrane results in a rejection of below 40%, advantageously of below 20%, advantageously of below 10%, advantageously of below 5% for the formed chiral amine product. It will be apparent for those skilled in the art that apart from the molecular weight (or size) of the amino donor, the transaminase, the unreacted amino acceptor (or unreacted ketone substrate) (if any), and the formed (co-)products, the retention by the membrane also depends on the (three-dimensional) shape (e.g. linear or globular), charge, structure and concentration of those molecules, as well as on their solubility parameters in the reaction solution (1) and/or second solution (2) (advantageously permeate solution).

Depending on the selected membrane, the MWCO can for example range between 150 to 300 g/mol, between 150 to 900 g/mol, between 180 to 1200 g/mol, between 280 to 600 g/mol, between 300 to 500 g/mol, or between 300 to 750 g/mol. Low molecular weight amino donors (having a molecular weight below 150 g/mol) as used in prior art transamination reactions would hence not be rejected by the membranes, and would pass through, thereby wasting excess (unreacted) amino donor substrate and contaminating the second solution (advantageously permeate solution). Further purification steps would therefore be needed, leading to low amine product purity. As in aspects of the present disclosure, to the contrary, HMW amino donors (having a molecular weight of at least 150 g/mol) or (LMW) amino donors being affixed on a support (the total molecular weight of the amino donor and the support being at least 150 g/mol) are used, such contamination of the second solution is avoided. The substrate cost is thereby lowered (as there is no waste of excess amino donor) and the cost for further recovery of the formed amine product is decreased (compared to prior art methods).

Advantageously, the porous membrane (3) is a nanofiltration membrane. Advantageously, the nanofiltration membrane is a polymeric or ceramic nanofiltration membrane. Advantageously, the membranes are chemically inert and exhibit high mechanical, thermal and hydrothermal stabilities, favoring a long term use.

More advantageously, the pore size of the pores of the porous membrane is lower than 1 µm. Advantageously, the pore size of the pores of the porous membrane ranges from 0.5 nm to 100 nm, advantageously from 0.5 nm to 50 nm, advantageously from 0.5 nm to 20 nm, advantageously from 1 nm to 10 nm (as measured by permporometry or nitrogen sorption techniques as known by the skilled person in the art).

In advantageous aspects of the disclosure, the membrane is selected based on its MWCO and/or pore size of the pores of the membrane so as to result in a rejection of at least 60%, advantageously of at least 80%, advantageously of at least 90%, advantageously of at least 95% for each of the amino donor, the transaminase, and the formed co-product. The MWCO and/or pore size of the pores of the membrane is also selected such that using the membrane results in a rejection of below 40%, advantageously of below 20%, advantageously of below 10%, advantageously of below 5% for the formed chiral amine product.

Suitable membranes for use in the membrane unit (8) will be apparent for those skilled in the art. Commercially available membranes such as Synder® NFX, Synder® NFW, NF-99-HF from Alfa Laval, DOW FILMTEC™ NF90, DESAL® DK NF, or the like can be used.

In advantageous aspects of the disclosure, the amino donor is provided in excess compared to the provided amount of amino acceptor so as to shift the thermodynamic equilibrium to the amine product side of the transamination reaction. As a consequence substantially all the available amount of amino acceptor present in the first solution (1) will react in the transamination reaction (leaving an excess amount of unreacted amino donor in the reaction solution, and no amount of unreacted amino acceptor). Only in case the transamination reaction would not be fully completed, unreacted amino acceptor will still be available in the reaction solution (1). Based on its molecular weight (similar to the molecular weight of the formed amine product) it will also pass through the selected membrane (3).

For example, using 2-bromo-4-acetylacetanilide (molecular weight about 256 g/mol) as ketone substrate, PEG-A (molecular weight about 400 g/mol) as HMW amino donor, and a porous membrane with a MWCO ranging from 280 to 600 g/mol: the formed amine product (molecular weight about 256 g/mol) in the reaction solution (1) will pass through the membrane (3) forming the second solution (2) (advantageously permeate solution) whereas excess amino donor (molecular weight about 400 g/mol) will be retained in the first solution (1) by the membrane (3). Unreacted ketosubstrate in the reaction solution, if any, will also be able to pass through the selected membrane (based on the molecular weight of the ketosubstrate, being similar to the molecular weight of the formed amine product) to the second solution.

Only in case unreacted amino acceptor (ketone substrate) passes through the membrane, the ketone substrate in the second solution is to be further separated from the formed amine product also collected therein. It is apparent for those skilled in the art that this purification (separation) is easy as ketone substrate and amine product do not have similar properties due to their different main functional groups. For example, solvent extraction can be performed for separating unreacted amino acceptor (ketone substrate) from the formed amine product (in that case thus both being present in the second solution). For instance, unreacted benzyl acetone substrate (amino acceptor) in the second solution can be further removed from said solution by extraction with t-butyl methyl ether, while the formed amine product 1M3P (1-methyl-3-phenylpropylamine) can be isolated from the second solution by extraction at pH 12 with t-butyl methyl ether followed by solvent evaporation at high vacuum.

The transamination reaction for producing (optically active) chiral amines, as used in the present disclosure, typically comprises the steps of:
  providing an amino acceptor and an amino donor;
  reacting the amino acceptor and the amino donor with a transaminase enzyme, such as a (R) or (S)-selective transaminase; and
  obtaining the desired (optically active) chiral amine and a co-product (ketone).

In the context of the present description, "transaminase" refers to a polypeptide with enzymatic activity capable of transferring an amino group ($-NH_2$), a pair of electrons, and a proton from a primary amine to a carbonyl group ($C=O$) of an acceptor molecule, using pyridoxal-phosphate (PLP) as a coenzyme in the transaminase reaction. Transaminases as used herein may be naturally occurring (wild type, non-engineered) transaminases, or non-naturally occurring transaminases generated by human manipulation or engineered, such as recombinant polypeptides or variant polypeptides engineered to have a modified or improved enzymatic activity. (R) or (S)-selective transaminases are capable of catalyzing the transfer of an amino group from an amino donor to an acceptor molecule, thereby forming R-specific or S-specific chiral amines, respectively. The transaminase as used herein can be in free form, immobilized on a suitable support or matrix such as cross-linked dextran or agarose, silica, polyamide, or cellulose, or encapsulated in polyacrylamide, alginates, fibers, or the like. The transaminase as used herein may be in the form of whole cells containing transaminase, or engineered whole cells acting as a host to transaminase. Methods for such immobilization or encapsulation are known to the skilled person. It will be apparent for those skilled in the art to select an appropriate transaminase depending on the desired chiral product, and the available substrates (i.e. the ketone acceptor and the amino donor). Transamination of the substrates can be carried out in a bioreactor using an aliquot of the enzyme with the substrate typically at a defined concentration. The reaction parameters such as pH, temperature, and mixing are maintained at levels that favor optimal biocatalytic activity and stability. The reaction can also be carried out in vivo by expression of the desired transaminase in a host. The desired host can, for example, be selected from the group of *Saccharomyces* sp., *Pichia* sp., *Hansenula* sp., *Arthrobacter* sp., *Pseudomonas* sp., *E. coli* sp. The described biotransformation process takes place in the host cell wherein the host cell expresses the desired enzyme for carboligation.

In advantageous aspects of the disclosure, the transaminases (also known as aminotransferases EC 2.6.1.18) can be obtained from various microorganisms. Advantageously, the transaminases are obtained from the organisms selected from the group consisting of *Achromobacter denitrificans, Achromobacter denitrificans* Y2k-2, *Aspergillus terreus, Bacillus cereus, Bacillus cereus* K-22, *Burkholderia cepacia, Chromobacterium violaceum, Escherichia coli, Ochrobactrum anthropi, Phaseolus vulgaris, Pseudomonas aeruginosa, Pseudomonas fluorescens, Rattus norvegicus, Vibrio fluvialis,* and *Vibrio fluvialis* JS17.

Advantageously, the transaminase is 3HMU from *Ruegeria pomeroyi* (i.e. aminotransferase class III from *Silici-*

*bacter pomeroy*), or 3FCR from *Ruegeria* sp. TM1040; advantageously, the transaminase is 3HMU from *Ruegeria pomeroyi*. These transaminases are expressed in *E. coli* BL21 (DE3) (purchased from e.g. Novagen®) as a host.

In aspects of the present disclosure, advantageously, the prochiral amino acceptor is a ketone substrate selected from the group consisting of acetophenone, ortho-bromoacetophenone, benzylacetone, and 2-bromo-4-acetylacetanilide;

the amino donor is selected from the group consisting of (highly flexible) poly(ethylene glycol) bis (3-aminopropyl); 1,4-bis(3-aminopropyl)piperazine; poly(propylene glycol) bis(2-aminopropyl ether) (PEG-A); O-(2-Aminopropyl)-O'-(2-methoxyethyl)polypropylene glycol (PEG-B); O,O'-Bis (2-aminopropyl) polypropylene glycol-block-polyethylene glycol-block-polypropylene glycol (PEG-C); and 1,2-bis(3-aminopropylamino)ethane; and the transaminase is 3HMU from *Ruegeria pomeroyi* or 3FCR from *Ruegeria* sp. TM1040, advantageously the transaminase is 3HMU from *Ruegeria pomeroyi*.

More advantageously, the prochiral amino acceptor is a ketone substrate selected from the group consisting of acetophenone, ortho-bromoacetophenone, benzylacetone, and 2-bromo-4-acetylacetanilide, advantageously benzylacetone;

the amino donor is poly(propylene glycol) bis(2-aminopropyl ether) (PEG-A) or O,O'-bis(2-aminopropyl) polypropylene glycol-block-polyethylene glycol-block-polypropylene glycol (PEG-C); and the transaminase is 3HMU from *Ruegeria pomeroyi* or 3FCR from *Ruegeria* sp. TM1040.

Even more advantageously, the prochiral amino acceptor is a ketone substrate selected from the group consisting of acetophenone, ortho-bromoacetophenone, benzylacetone, and 2-bromo-4-acetylacetanilide, advantageously benzylacetone;

the amino donor is poly(propylene glycol) bis(2-aminopropyl ether) (PEG-A) or O,O'-bis(2-aminopropyl) polypropylene glycol-block-polyethylene glycol-block-polypropylene glycol (PEG-C); and the transaminase is 3HMU from *Ruegeria pomeroyi*.

Most advantageously, the prochiral amino acceptor is a ketone substrate selected from the group consisting of acetophenone, ortho-bromoacetophenone, benzylacetone, and 2-bromo-4-acetylacetanilide, advantageously benzylacetone;

the amino donor is poly(propylene glycol) bis(2-aminopropyl ether) (PEG-A); and the transaminase is 3HMU from *Ruegeria pomeroyi*.

Alternatively and most advantageously, the prochiral amino acceptor is a ketone substrate selected from the group consisting of acetophenone, ortho-bromoacetophenone, benzylacetone, and 2-bromo-4-acetylacetanilide, advantageously benzylacetone;

the amino donor is O,O'-Bis(2-aminopropyl) polypropylene glycol-block-polyethylene glycol-block-polypropylene glycol (PEG-C); and the transaminase is 3HMU from *Ruegeria pomeroyi*.

The amine products produced by methods of aspects of the disclosure can be further used as an intermediate in the synthesis of a pharmaceutical product.

In embodiments of aspects of the disclosure, the method is performed using a chiral amine production and separation unit. Such a unit (4) is schematically represented in FIG. 3. A unit (or device) (4) for producing and subsequently separating (recovering) a chiral amine comprises:

a first vessel (5) for holding an amino donor and a prochiral amino acceptor, the first vessel (5) being in fluid connection with an enzyme tank (6) for holding a first solution (1) (i.e. the reaction solution of the transamination reaction between amino donor and prochiral amino acceptor in the presence of a transaminase thereby forming a chiral amine and a co-product), and a valve (12) being arranged between the first vessel (5) and the enzyme tank (6);

optionally a second vessel (7) for holding an inert gas being in fluid connection with the enzyme tank (6) and a means for providing a flow of inert gas to the enzyme tank (6);

a membrane unit (8) arranged downstream from the enzyme tank (6), said membrane unit (8) being in fluid connection with the enzyme tank (6), and said membrane unit (8) comprising a first compartment (9) separated by a porous membrane (3) from a second compartment (10), and a (three-way) valve (11) being arranged between the enzyme tank (6) and the (first compartment (9) of the) membrane unit (8);

the first compartment (9) of the membrane unit (8) is configured for receiving the first solution (1) (comprising the formed chiral amine) from the enzyme tank (6), the second compartment (10) is configured for holding a second solution (2), advantageously the second solution (2) is the permeate (or filtrate) of the first solution (formed by permeating the chiral amine from the first solution (1) across the porous membrane (3));

a third vessel (13) for recovering (collecting) the formed amine product, said third vessel (13) being arranged downstream from the membrane unit (8), said third vessel (13) being in fluid connection with the second compartment (10) of the membrane unit (8);

optionally a means for recirculating the first solution (1) (advantageously comprising excess donor amine) from the first compartment (9) of the membrane unit (8) back into the enzyme tank (6) (e.g. via circulation pump P-2 in FIG. 3).

Advantageously, the porous membrane is a nanofiltration membrane, advantageously, a polymeric or ceramic nanofiltration membrane.

Advantageously, the porous membrane has a MWCO for amino donor and transaminase of at least 150 g/mol (advantageously of at least 200 g/mol, advantageously of at least 300 g/mol), and/or the pore size of the pores of the porous membrane ranges from 0.5 nm to 100 nm (advantageously from 0.5 nm to 50 nm, advantageously from 0.5 nm to 20 nm, advantageously from 1 nm to 10 nm).

Advantageously, the unit (4) comprises a means for applying a pressure across the porous membrane (3).

More specifically, referring to FIG. 3, a first vessel (5) is in fluid connection with an enzyme tank (6) (P-1 in FIG. 3 is a diafiltration pump). The amino donor and the prochiral amino acceptor are fed from the first vessel (5) to the enzyme tank (6) wherein the reaction takes place in a first solution (1) in the presence of a transaminase enzyme (and optionally in the presence of an inert gas, such as $N_2$-gas, fed from a second vessel (7) to the enzyme tank (6), the second vessel (7) being in fluid connection with the enzyme tank (6)), thereby forming a chiral amine and a co-product. The amino donor is a high molecular weight (HMW) amino donor, the molecular weight of the high molecular weight amino donor being at least 150 g/mol (advantageously at least 200 g/mol, advantageously at least 300 g/mol); or the amino donor is affixed on (linked to, immobilized on) a (inert) support, the total molecular weight of the amino donor and the support being at least 150 g/mol (advantageously at least 200 g/mol, advantageously at least 300 g/mol). Advantageously, the amino donor (or the amino donor affixed to a support) is provided in excess (with respect to the amount of amino acceptor provided). Alternatively, the amino donor and amino acceptor are provided in equimolar amount at subsequent intervals (a valve (12) is thereto arranged between the first vessel (5) and the enzyme tank (6)). A membrane unit (8) is in fluid connection with the enzyme tank (6) (the membrane unit (8) being downstream from the enzyme tank (6)). In the membrane unit (8) following the enzyme tank (6), the separation of the chiral amine product formed in the transaminase reaction in the first solution (1) will take place. The membrane unit (8) comprises a first compartment (9) separated by a porous membrane (3) from a second compartment (10). Advantageously, the membrane (3) is selected based on its MWCO (and/or pore size) so as to only enable the formed amine product to pass through the membrane (3). The first solution (1) (reaction solution of the transamination reaction comprising the formed chiral amine) is fed to the first compartment (9) of the membrane unit (8). The chiral amine is separated from the first solution (1) using the porous membrane (3) (i.e. by membrane separation). The first solution (1) comprising the formed chiral amine is thereby contacted with the porous membrane (3). Advantageously, the first solution (1) comprising the formed chiral amine is forced to pass through the porous membrane (3) by applying a pressure across the porous membrane (3), advantageously by applying a pressure between 5 to 30 bar. The chiral amine product, formed in the transamination reaction in solution (1) in enzyme tank (6), will thereby be extracted (advantageously permeated) from the first solution (1) across the porous membrane (3) forming a second solution (2) (advantageously permeate solution). Based on the high molecular weight of the amino donor and the MWCO (and/or pore size) of the selected membrane (3), excess (unreacted) amino donor cannot pass through the porous membrane (3). The transaminase, due to his high molecular weight, will be retained in the first compartment (9) by the porous membrane (3) as well. As such, (the fraction of) the first solution (1) that does not pass through the membrane (3) comprising amino donor in excess can be recirculated from the first compartment (9) of the membrane unit (8) into the enzyme tank (6) for further transamination reaction with newly supplied amino acceptor from the first vessel (5). Hence, no excess amino donor will be lost in the transamination reaction. Furthermore, as in the transamination reaction the amino acceptor forms a high molecular weight co-product, the latter will also be retained by the selected porous membrane (3) with appropriate MWCO value (and/or pore size). As such, the co-product remains in the first solution (1) where it is accumulated. Without wishing to be bound by theory, it is believed that the accumulated co-product in the first solution (1) will polymerize and will hence contribute to (or even enhance) the shifting of the thermodynamic equilibrium of the transamination reaction to the amine product side. On the other hand, based on its low molecular weight and the MWCO (and/or pore size) of the selected membrane (3), the formed chiral amine product will pass through the membrane (3) and can be recovered from the second compartment (10) of the membrane unit (8). Moreover, as the second solution (2) (advantageously permeate solution) is not contaminated with excess (unreacted) amino donor, the formed chiral amine can be recovered from second solution (2) with high product purity. The recovered amine can be collected in a third vessel (13) being arranged downstream from the membrane unit (8) and being in fluid connection with the second compartment (10) thereof. The production and separation of the chiral amine can be performed in continuous or in batch mode (the latter by adding (arranging) a (three-way) valve (11) between the enzyme tank (6) and the (first compartment (9) of the) membrane unit (8)). As advantageously the amino donor is provided in excess compared to the provided amount of amino acceptor, or alternatively, the amino donor and amino acceptor are provided in equimolar amount, substantially all the available amount of amino acceptor will have reacted in the transamination reaction. Unreacted amino acceptor, if still any (for example in case the transamination reaction would not be fully completed), will also pass through the membrane (3), together with the formed amine product. Only in the latter case, a further (easy) purification step is to be performed to separate amine product and amino acceptor in the second solution.

EXAMPLES

In the examples, all chemicals were of analytical grade purity and obtained from Sigma Aldrich.

Example 1: Large Amino Donors in Transamination Reactions

The HMW amino donors listed in Table 1 were tested in a feasibility study for reaction with TA enzymes (the HMW amino donors being commercially available and relatively cheap). More particularly, in this study the acceptance of HMW amino donors by TA enzymes was investigated running a glycine oxidase assay (as described by Weiß et al. in Anal. Chem. 2014, 86, 11847-11853). Thereto, 25 wild type transaminases were selected from a library of enzymes. Transaminase selection was made on the basis of TAs availability, broad substrate and amino donor scope, and stability. Table 2A lists the selected transaminases. Among the 25 enzymes tested, two wild type TAs accepted the high molecular weight amino donors listed in Table 1 as substrates. More particularly, among the transaminases tested, the ((S)-selective) TA enzyme 3HMU (denoted as TA_3HMU, aminotransferase class III from Silicibacter pomeroy) turned out to be the most active enzyme when performing the glycine oxidase assay with the HMW amino donors listed in Table 1. Also the TA enzyme 3FCR (denoted as TA_3FCR) was active with these HMW amino donors. The best acceptance observed was the combination of the transaminase TA_3HMU with the amino donors PEG-A and PEG-C.

TABLE 1

HMW amino donors tested for reaction with TA enzymes

| Structure | Commercial name | Abbreviation | MW (g/mol) |
|---|---|---|---|
| $H_2N\text{-}(CH_2)_3\text{-}O\text{-}[CH_2CH_2O]_n\text{-}(CH_2)_3\text{-}NH_2$ | (highly flexible) poly(ethylene glycol) bis (3-aminopropyl) | 1916 (or AD 7) | 1500 |
| 1,4-Bis(3-aminopropyl)piperazine structure | 1,4-Bis(3-aminopropyl)piperazine | 1914 (or AD 2) | 200 |
| Poly(propylene glycol) bis(2-aminopropyl ether) structure | Poly(propylene glycol) bis(2-aminopropyl ether) | PEG-A (or AD 3) | 400 |
| O-(2-aminopropyl)-O'-(2-methoxyethyl)polypropylene glycol structure | O-(2-aminopropyl)-O'-(2-methoxyethyl)polypropylene glycol | PEG-B (or AD 4) | 600 |
| O,O'-bis(2-aminopropyl) polypropylene glycol-block-polyethylene glycol-block-polypropylene glycol structure | O,O'-bis(2-aminopropyl) polypropylene glycol-block-polyethylene glycol-block-polypropylene glycol | PEG-C (or AD 6) | 600 |
| $H_2N\text{-}(CH_2)_3\text{-}NH\text{-}(CH_2)_2\text{-}NH\text{-}(CH_2)_3\text{-}NH_2$ | 1,2-bis(3-aminopropylamino)ethane | 1913 (or AD 1) | 174 |
| AD 5 dendrimer structure | | AD 5 | 516 |

TABLE 2A

Different TAs expressed in *E. coli* BL21 (DE3) tested through the glycine oxidase assay

| Name | Species |
|---|---|
| AspFum | *Aspergillus fumigatus* |
| AspOry | *Aspergillus oryzae* |
| AspTe | *Aspergillus terreus* |
| GibZea | *Gibberella zeae* |
| MycVan | *Mycobacterium vanbaalenii* |
| NeoFis | *Neosartorya fisheri* |
| PenChr | *Penicillium chrysogenum* |
| BurSp | *Burkholderia* sp. |
| RhiEtli | *Rhizobium etli* |
| HypNep | *Hyphomonas neptumium* |
| GamPro | *Gamma proteobacterium* |
| LabAle | *Labrenzia alexandrii* |
| JanSp | *Jannaschia* |
| MarSp | *Marimonas* sp. |
| MesLoti | *Mesorhizobium loti* (13) |
| MesLot | *Mesorhizobium loti* (14) |
| RosSp | *Roseobacter* sp. |
| RhoFer | *Rhodoferax ferrireducens* |
| ATA117 | *Arthrobacter* sp. |
| 3GJU | *Mesorhizobium loti* maff303099 |
| 3FCR | *Ruegeria* sp. TM1040 |
| 3HMU | *Ruegeria pomeroyi* |
| 3I5T | *Rhodobacter sphaeroides* |
| 2YKY | *Mesorhizobium* sp. strain LUK |
| Vfl | *Vibrio fluvialis* JS17 |

Among the different reaction conditions tested, FIG. 4.1 summarizes the results obtained with the best TA enzyme (i.e. TA_3HMU) when using the selected amino donors listed in Table 1. More particularly, FIG. 4.1 shows the increase of absorbance at 498 nm at 37° C. over time for TA_3HMU when using different amino donors (right side of FIG. 4.1) and experimental slopes obtained (left side of FIG. 4.1). Final substrate concentration amounted to 2.5 mM glyoxylate, 20 mM large amino donor, 7.28 U/mL horseradish peroxidase, 0.12 mg/mL purified glycine oxidase, 3 mM 4-amino antipyrine, and 4.7 mM vanillic acid in CHES buffer (100 mM) with pH 9.5, in total reaction volumes of 150 μL. Cells with empty pET28a(+) vector were applied as negative control. A reaction using 2.5 mM α-MBA was applied as positive control.

The above (photometric) assay is semiquantitative: the increasing absorbance (slope in FIG. 4.1) correlates with enzyme activity. An accurate quantification, however, was difficult to be performed as the assay is a multi-enzyme reaction. Nevertheless, the trends and the experimental slope obtained in FIG. 4.1 showed that HMW amino donors are well accepted by TA_3HMU. Moreover, no severe inhibition effects of the large amino donor molecules could be observed at the concentrations used in the biocatalysis experiments. The activity of almost all the tested large amino donor is indeed comparable to the activity of the positive control α-MBA (1-phenylethylamine) which is, among model amino donors, the easiest to be deaminated (cf. Guo et al. in Green Chem., 2017, 19, 333-360).

Table 2B reports the results of the TA screening towards HMW AD 1-7, α-MBA was applied as positive control. A first screening focused on evaluating 7 wild type biocatalysts (as listed in the table) with AD 1, 2, 5 and 7. Under the experimental condition tested, it can indeed be observed that the (S)-selective TA from *Silicibacter pomeroy* (TA_3HMU) exhibited high activity in presence of AD 2 and AD 7. Only modest activity was observed with the other tested enzymes. TA_3HMU was then further tested with three commercially available HMW Jeffamines® (AD 3, 4 and 6). In contrast to the other tested large ADs, these molecules possess a typical polyethylene glycol backbone. TA_3HMU activities resulted indeed to be broadly comparable to those achieved with the positive control a-MBA amine donor. FIG. 4.2 depicts the results summarized in Table 2B (where the result for AD 5 is also included, compared to FIG. 4.1), the results being obtained with identical conditions as discussed for FIG. 4.1 hereinabove).

TABLE 2B

TA screening towards HMW AD 1-7, α-MBA was applied as positive control

|  |  |  | AD 1 | AD 2 | AD 3 | AD 4 | AD 5 | AD 6 | AD 7 | α-MBA |
|---|---|---|---|---|---|---|---|---|---|---|
| Wildtype TA | (R)- (S)-Selective | AspFum | 0 | 0 | n.d. | n.d. | 0 | n.d. | 0 | + |
|  |  | 3FCR | 0 | ++ | n.d. | n.d. | 0 | n.d. | + | + |
|  |  | 3HMU | 0 | +++ | ++++ | +++ | 0 | ++++ | +++ | ++++ |
|  |  | ATA 117 | 0 | + | n.d. | n.d. | 0 | n.d. | + | + |
|  |  | Vfl | 0 | + | n.d. | n.d. | 0 | n.d. | 0 | ++ |
|  |  | AspOry | 0 | + | n.d. | n.d. | 0 | n.d. | 0 | 0 |
|  |  | MycVan | 0 | 0 | n.d. | n.d. | 0 | n.d. | 0 | 0 | n.d.: not determined (not tested);
0: no activity detected

In view of the above, it has been demonstrated that large (or HMW) amino donors are well accepted by transaminase enzymes. Hence, the HMW molecules can be used in transamination reactions for the asymmetric synthesis of industrial interesting chiral amines.

Example 2: Amino Acceptor Substrates in Transamination Reactions

For performing a transaminase reaction to obtain industrial important chiral amines, the TA enzyme has to well accept the amino donor but also the amino acceptor substrates (i.e. the ketosubstrates). Thereto, substrates from Substrate Class I (difficult substrates from thermodynamic point of view) were considered for reaction with TA enzymes. The Substrate Class I ketosubstrates are listed in Table 3A.

TABLE 3A

Substrate Class I ketosubstrates

| Structure | name | MW (g/mol) |
|---|---|---|
| 1a | acetophenone | 120 |
| 1b | ortho-bromoacetophenone | 199 |
| 1c | benzylacetone | 148 |
| 1d | 2-bromo-4-acetylacetanilide | 256 |

Asymmetric synthesis of chiral amines were performed using HMW amino donors and substrates 1a, 1b and 1c in the presence of TA_3HMU enzyme. Product formation was qualitatively detected for all the reactions tested either through TLC analysis or by chiral GC analysis. Substrates 1a and 1b were difficult to be aminated without applying a strategy of equilibrium shifting and very low product formation was detected. However, performing the transamination reaction using substrates 1a or 1b, followed by a separation of the formed amine product using a membrane unit (8), according to advantageous aspects of the disclosure, will further shift the thermodynamic equilibrium to the product side of the reaction, thereby improving the product purity of the produced amine product.

For subsequent studies on the transamination reaction, only the ketone substrate 1c (benzylacetone, abbreviated BA) was used due to its relative ease of transamination (compared to acetophenone) (cf. FIG. 4.3, showing a model transamination reaction, BA being the amino acceptor, AD 6 (cf. Table 1) being employed as amine donor therein). It is expected that, due to their similar main ketone functional group, other ketosubstrates, advantageously the ketosubstrates listed in Table 3A, will behave in the same way as substrate 1c. Furthermore, based on the results obtained in example 1 and on economical evaluations (the amino donors being cheap in purchase), only the HMW amino donors PEG-A and PEG-C were selected for further optimization. Here as well, it is expected that, due to their HMW and similar main amino functional groups, other HMW amino donors, advantageously the HMW amino donors listed in Table 1, will react in the same way as the PEGs.

Asymmetric amine synthesis experiments were performed using freeze-dried crude extract of TA_3HMU, provided by the company Enzymicals (Germany) and using PEG-A and PEG-C as amino donors (the activity of the enzyme being 970 mU/mg, photometric assay based on acetophenone detection). For a first test, a quite high amount of enzyme (12.5 mg/mL freeze dried powder, corresponding to about 6 mg/mL of total protein content) was used. In addition to poly ethylene glycol molecules (PEGs), the common and cheap LMW amino donor IPA was also investigated. Unlike PEGs, which can be retained by a porous (nanofiltration) membrane (3) with appropriate MWCO and/or pore size, the LMW amino donor IPA will also permeate forming the second solution (2). The trends obtained when running the transamination reaction are shown in FIG. 5.1.

Asymmetric amine synthesis experiments were also performed using amine transaminases TA_v2, purchased from c-LEcta GmbH, Leipzig, Germany. The purified enzyme was supplied as freeze-dried powder, the activity of TA_v2 being 1.73 U/mg. All reactions were performed in 1 mL volume containing 12.5-0.78 mg/mL of either TA_3HMU or TA_v2 powder, 10-500 mM amine donor (IPA, PEG-A and PEG-C, 10 mM BA model substrate (dissolved in DMSO) and 0.1 mM PLP in 100 mM CHES buffer, pH 9.5. The final DSMO concentration was 5% (v/v). While incubating at 30° C. and 1000 rpm, samples (500 μL) were taken after distinct time periods, supplemented with 25 μL of trifluoroacetic acid (TFA) and prepared for Ultra-Performance Liquid Chromatography (UPLC).

Substrate (BA) and product (MPPA) concentrations were determined by UHPLC (Thermo Scientific™) with UV detection at 194/210 nm. The chromatographic separation was achieved using 1 μL injection onto a C18 reversed-phase column (Waters Acquity UPLC® BEH C18 1.7 μm 2.1×50 mm). The column temperature was kept at 40° C. The gradient elution program is using mobile phase A 0.1% Formic Acid (FA) in Water (dH2O) and mobile phase B 0.1% FA in acetonitrile (ACN). The elution program was as follows: 0-4 min 99-30% A; 4-5 min 30-1% A; 5-5.1 min 1-99% A; 5.1-7.5 min 99% A; all at a flowrate of 400 μL/min. Amine donors AD 3 and AD 6 were analysed by HPLC with ELSD detector on Alltima HP C18 HL 5 μ, 4.6×250 mm. The eluents for PEGs analysis were: A) dH2O, 0.1% FA; B) ACN, 0.1% FA.

Furthermore, tests were conducted using different loadings of freeze-dried crude extract of TA_3HMU. Since the biotransformation could not be observed photometrically, continuous time-dependent following of the enzyme reaction was not possible. Therefore, laborious stopped enzyme assay providing only few measure points had to be employed. As expected, the initial reaction rate decreased when the enzyme loading was reduced. In presence of IPA donor amine, higher conversions were achieved. However, the reaction end-point decreased, reducing the enzyme amount (cf. FIG. 5.2c). FIG. 5.2b shows TA_3HMU stability in presence of AD 6. Experimental conditions in FIG. 5.2: 10 mM BA; 250 mM AD; 0.1 mM PLP; 5% DMSO; 100 mM CHES buffer, pH 9.5, 30° C., 1000 rpm.

As already discussed hereinabove, using IPA as amine donor in transaminase reactions, a very high amount (e.g. 50-100 fold) amine donor excess is required, complicating downstream processing and possibly hampering the stability and activity of TAs (cf. e.g. Slabu, I. et al. in Catal. Today 306, 96-101 (2018); Savile, C. K. et al. in Science 329, 305-9 (2010); Dawood, A. W. H. et al. in ChemCatChem 10, 951-955 (2018)). TA_3HMU stability towards IPA and HMW ADs 3 and 6 was therefore explored. As expected, TA_3HMU fast inactivated in presence of IPA (cf. FIG. 5.3c), hence confirming that this amine donor, provided in 25-fold excess, hampers TA_3HMU stability and activity. In contrast to IPA, in presence of bulky donor amines (cf. FIG. 5.3a and FIG. 5.3b). Experimental conditions in FIG. 5.3: 10 mM BA; 250 mM amine donor (AD 3, AD 6 or IPA); 0.1 mM PLP; 5% DMSO; 100 mM CHES buffer, pH 9.5, 30° C., 1000 rpm. 3.125 mg/mL enzyme was used. Fresh enzyme was added after 72 hours of asymmetric synthesis reaction. TA_3HMU resulted to be active till reaction completion. Enzyme stability in presence of the tested Jeffamines® could be connected to the intrinsic nature of these difunctional primary amines, characterized by repeating oxypropylene units in the backbone. The polyethylene glycol backbone chain of the selected HMW amine donors, useful in a variety of polymers because of the hydrophilicity and flexibility imparted, might have enhanced enzyme activity and stability.

As already mentioned hereinabove, the solvent resistant TA_v2 was also tested in addition to TA_3HMU. Surprisingly TA_v2, which has been recently engineered for working at high IPA concentrations (cf. Borner, T. et al. in ChemBioChem 18, 1482-1486 (2017), resulted to be active and stable also when using HMW amine donors. As shown in FIG. 5.3 (white dots), TA_v2 enzyme outperformed TA_3HMU in terms of final conversions and reaction rates. In this latter regard, the enzyme formulation, in terms of purity, could have played a big role and an accurate comparison could be made when both enzymes are employed in purified form. Nevertheless for industrial applications, employing purified enzymes leads to additional operational costs. By providing 25 times excess of HMW amine donors, conversion around 45% and 65% were achieved employing crude extract lyophilized powder TA_3HMU and heat purified lyophilized TA_v2, respectively (cf. FIG. 5.4a). In FIG. 5.4, these results are compared with previous studies where diverse smart amine donors were used for thermodynamic equilibrium shifting (cf. FIG. 5.4b-e).

With the exception of the synthetic diamines 1a and 2a, which tremendously displaced the equilibria of TA reactions by spontaneous cyclisation and subsequent ring aromatisation of the co-product, considerably lower conversions were achieved with all the other smart amine donors (FIG. 5.4). However, diamines such as o-xylylenediamine (1a) (cf. Green et al. in Angew. Chem. Int. Ed. Engl. 2014 Sep. 26; 53 (40): 10714-7) or but-2-ene-1,4-diamine (2a) (cf. Martínez-Montero, L. et al. in Adv. Synth. Catal. 358, 1618-1624 (2016)) are usually expensive, highly toxic and form polymers difficult to remove, hence adding downstream processing costs. The alternative biogenic terminal diamines 3a, 4a and 5a, which require near stoichiometric donor loadings, were found to afford high conversions of a broad range of substrates. For ortho-substituted ketone substrates, the stabilizing interaction between the formed amine product and the halogen atom, drove the reactions to almost completion (cf. Galman, J. L. et al. in Green Chem. 19, 361-366 (2017))

whereas considerably lower non-activated ketones conversions were achieved (FIG. 5.4c). The acceptance of vicinal 1,2 diamines 6-8a by TA_3HMU enzyme was recently explored. Thermodynamic equilibrium could be shifted on the product side by spontaneous dimerization and subsequent oxidative aromatization (cf. Payer et al. in *European J. Org. Chem.* 2017, 2553-2559 (2017)). However, even employing 20 mg/mL TA_3HMU, BA was poorly converted (FIG. 5.4d). Remarkably, by using only 3 mg/mL of crude extract TA_3HMU, HMW AD 3 or AD 6 drove BA conversion to 45% and 51%, respectively.

Example 3: Effect of Amino Donor Loading

To demonstrate the benefits (for thermodynamic equilibrium shifting of the model reaction) of conducting transamination using excess of amino donors, the effect of amino donor loading was investigated. For this set of experiments, the TA_3HMU crude extract powder concentration was set to 3.125 mg/mL. The trends obtained when running the transamination reaction with different amino donor loading are shown in FIGS. 6 to 8.

Figure 6:
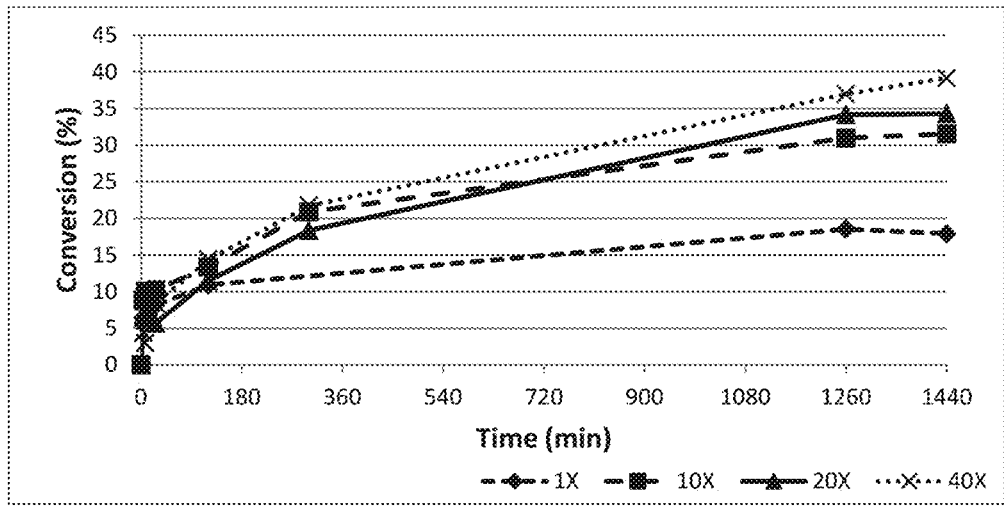
Figure 7:
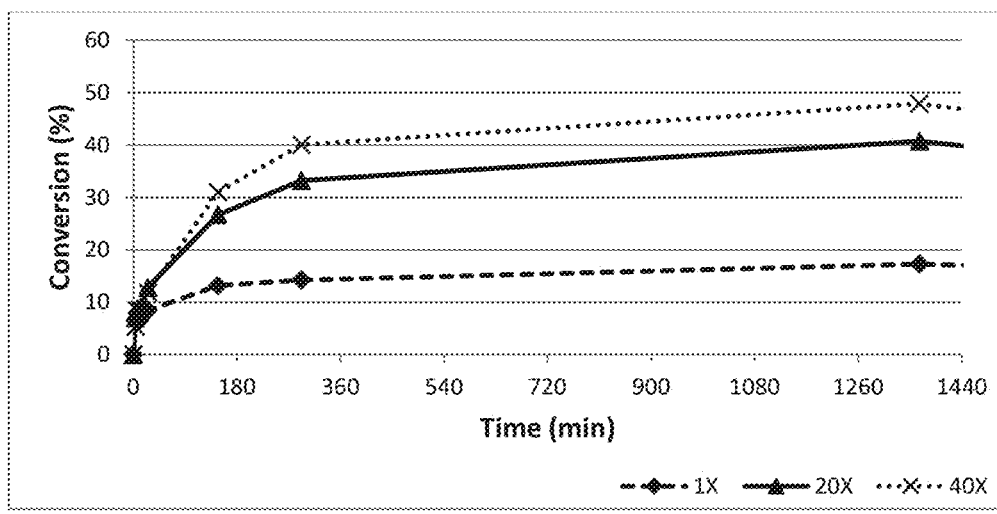
Figure 8:
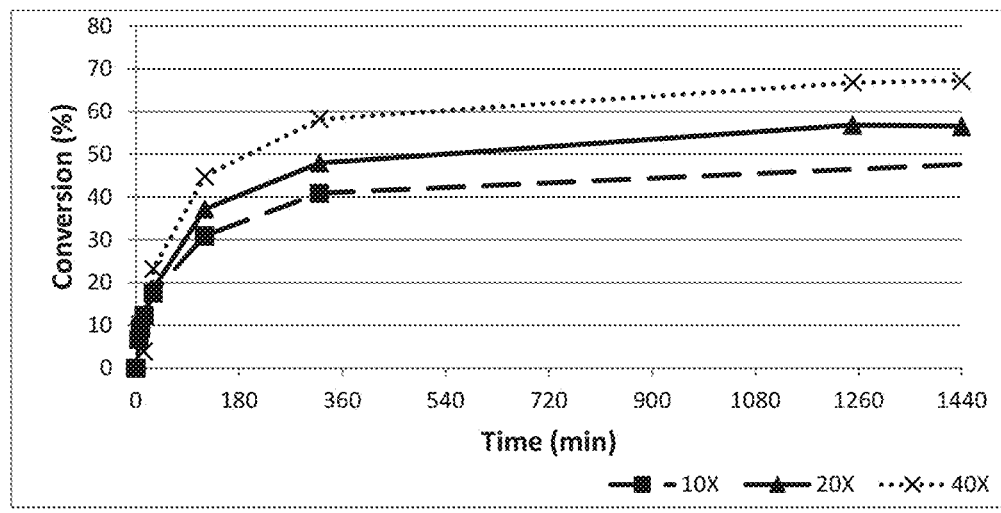
FIG. 8 shows the conversion of substrate BA in function of time when using different LMW amino donor IPA loadings.

FIG. 6, FIG. 7 and FIG. 8 show the BA conversion in function of time when using different amino donor loadings. Experimental Conditions: 10 mM BA; 10 mM AD (1×); 100 mM AD (10×); 200 mM AD (20×); 400 mM AD (40×); 0.1 mM PLP; 5% DMSO; 3.125 mg/mL lyophilized crude extract TA_3HMU; 100 mM CHES buffer, pH 9.5, 30° C., 1000 rpm.

Figure 9:
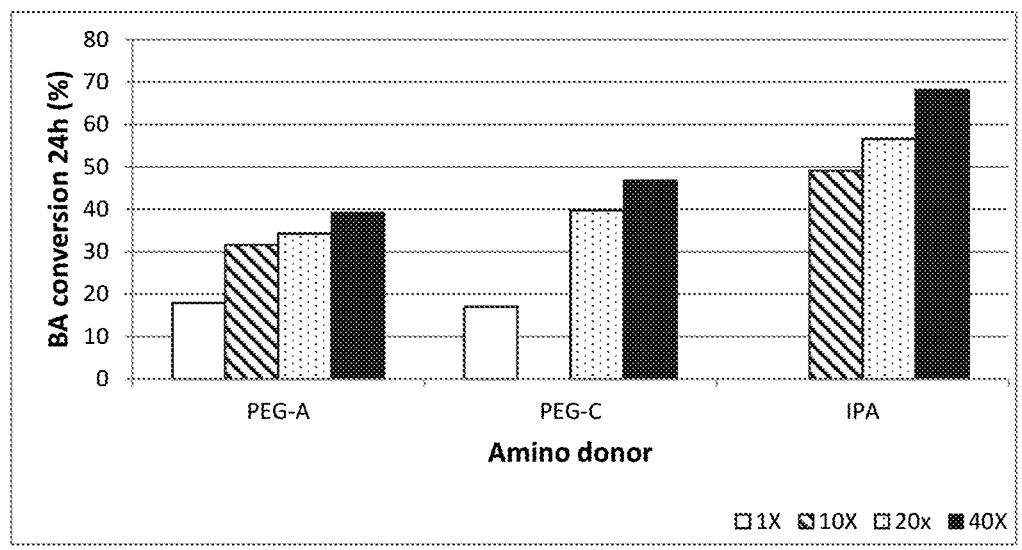
FIG. 9.1 shows the conversion of substrate BA after 24 h reaction when using different HMW or LMW amino donor loadings.

FIG. 9.1 shows the substrate BA conversion after 24 h reaction when using different amino donor loadings.

As expected, an excess of amino donor shifted the equilibrium to the product side. The reaction rate increased, increasing the amino donor amount (FIGS. 6 to 8) as well as the final conversion (FIG. 9.1).

Also for enzyme TA_v2 different amine donor loadings were explored.

As expected as well, an excess of HMW amines on TA_v2 enzymes boosted the equilibrium on the product side (comparing FIG. 9.2 for TA_3HMU with FIG. 9.3 for TA_v2), enhancing higher reaction rates (cf. FIG. 9.3). In contrast to IPA, the large AD 3 and 6 are viscous and more important, sterically bulky. Therefore, working with high HMW AD excess is not beneficial and for the subsequent experiments the amine donor concentration was set to 250 mM (25 times excess).

Example 4: Membrane Screening and Off Line Tests

Several commercial available porous, nanofiltration membranes were tested (thereby investigating their separation performances). More particularly, the ability of the membranes to reject HMW amino donors PEG-A and PEG-C was evaluated.

Aqueous solutions (300 mL) of PEG-A and PEG-C were prepared. 250 mM HMW PEG-A or PEG-C was thereto dissolved in 100 mM CHES buffer at pH 9.5. A high pressure stainless steel cross-flow membrane (filtration) unit was used. The test unit basically consisted of a feed vessel (capacity of approximately 1 L), a gear pump for circulation, and a rectangular membrane housing. In the membrane unit, the following commercially available nanofiltration membranes were used: Synder® NFX, Synder® NFW, DuraMem® 200, SolSep NF010206, GE KH Duracid, DESAL® DK NF, NF-99-HF from Alfa Laval, DOW FILMTEC™ NF90, PuraMem® Flux, PuraMem® Performance, and PuraMem® Selective. The tests were performed at room temperature. The permeate passing through the membrane was thereby collected in a recipient placed on a balance. Samples of permeate and retentate (the latter being the solution rejected (retained) by the membrane, i.e. not passing through the membrane) were taken at steady-state conditions (stable flux), and membrane rejections were calculated as follows:

$$R\ (\%) = \left(1 - \frac{C_p}{C_r}\right) * 100$$

where $C_p$ and $C_r$ denote the measured concentration of amino donor in the permeate and retentate, respectively.

Figure 10:
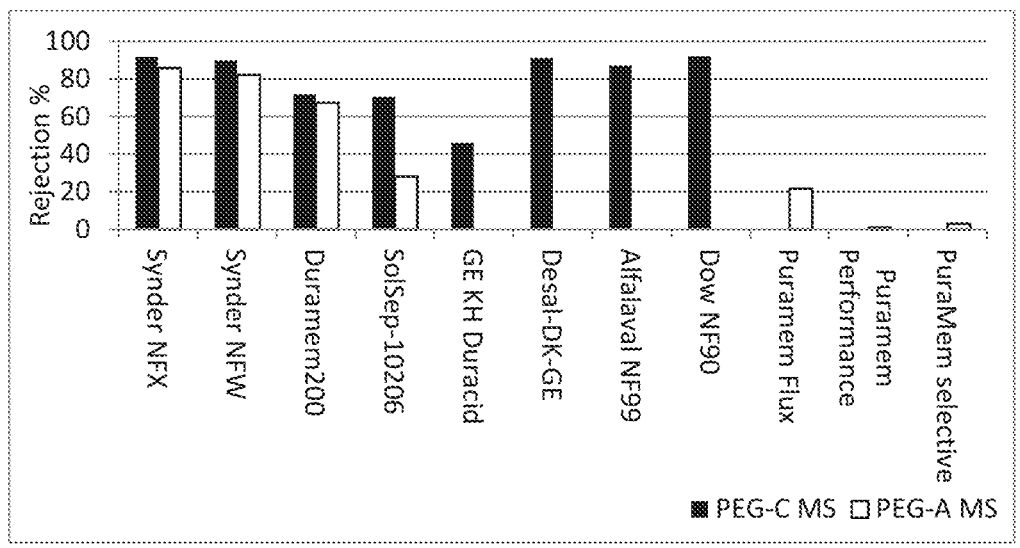
Figure 11:
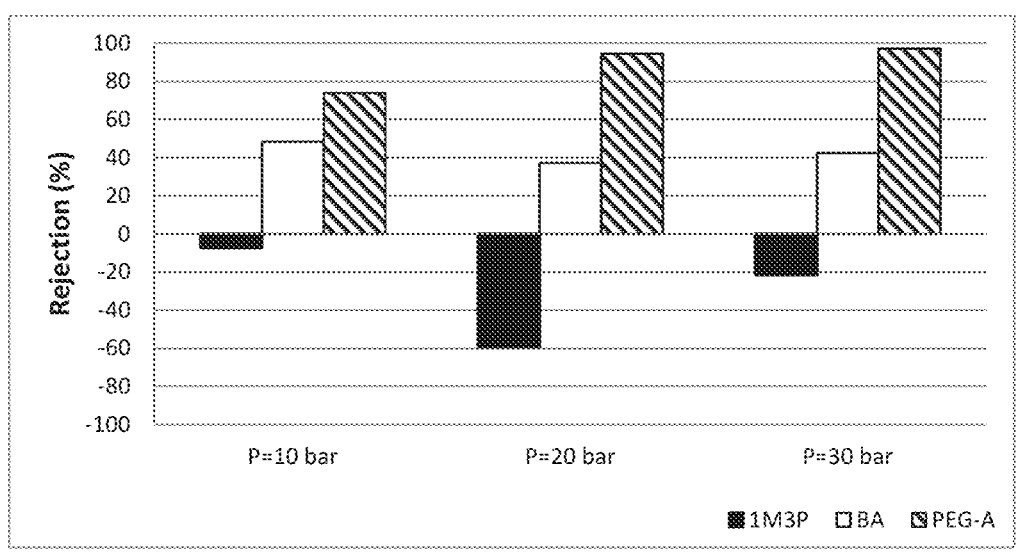
Figure 12:
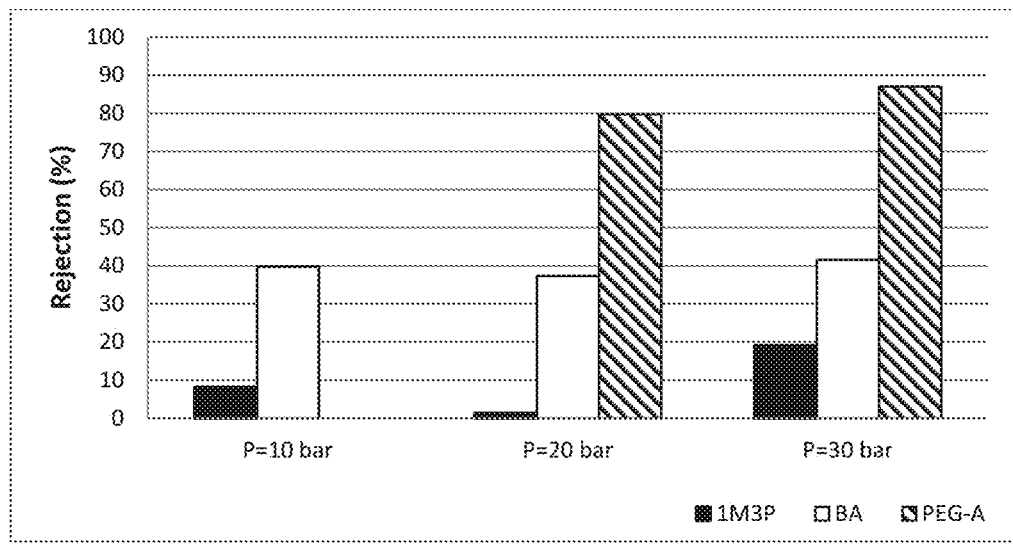
Figure 13:
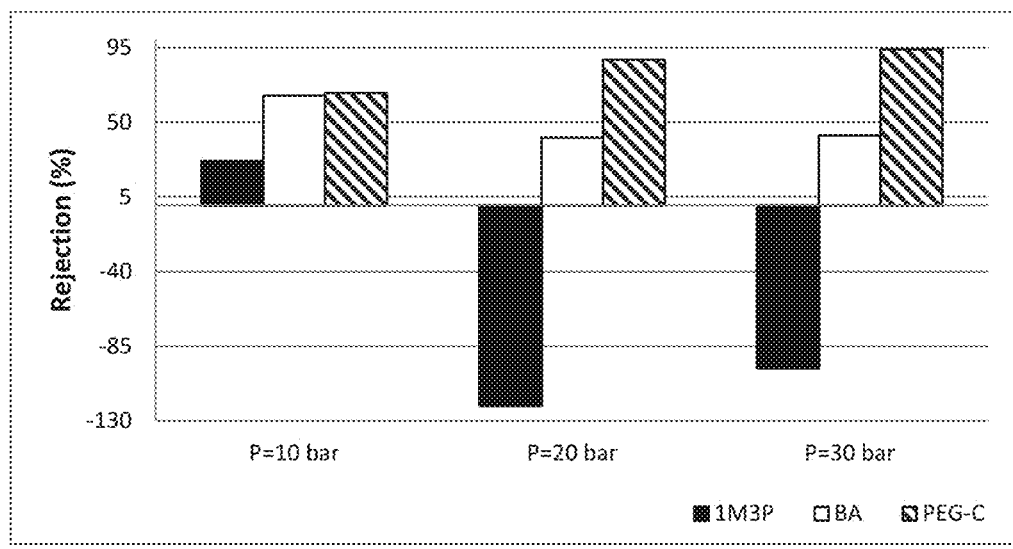
Figure 14:
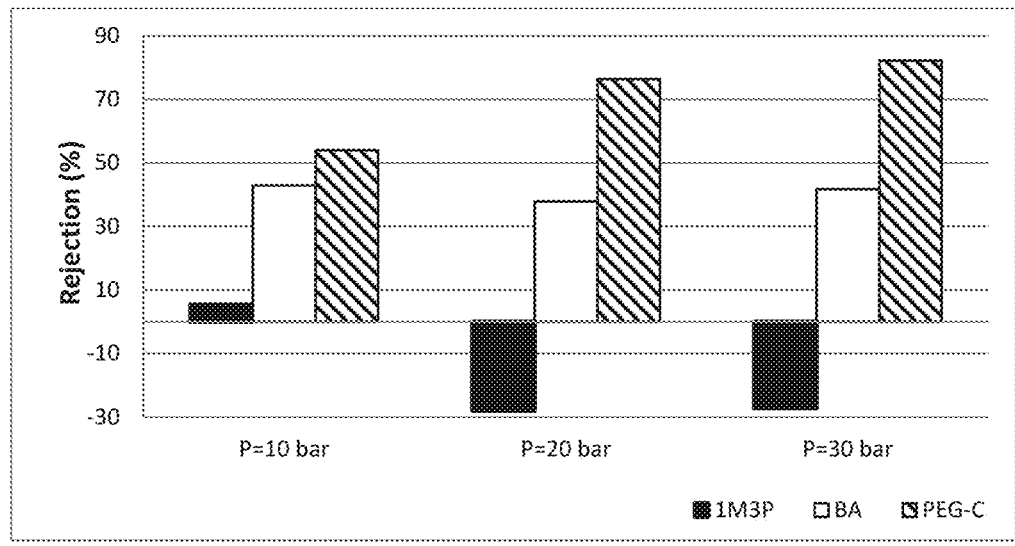
Figure 15:
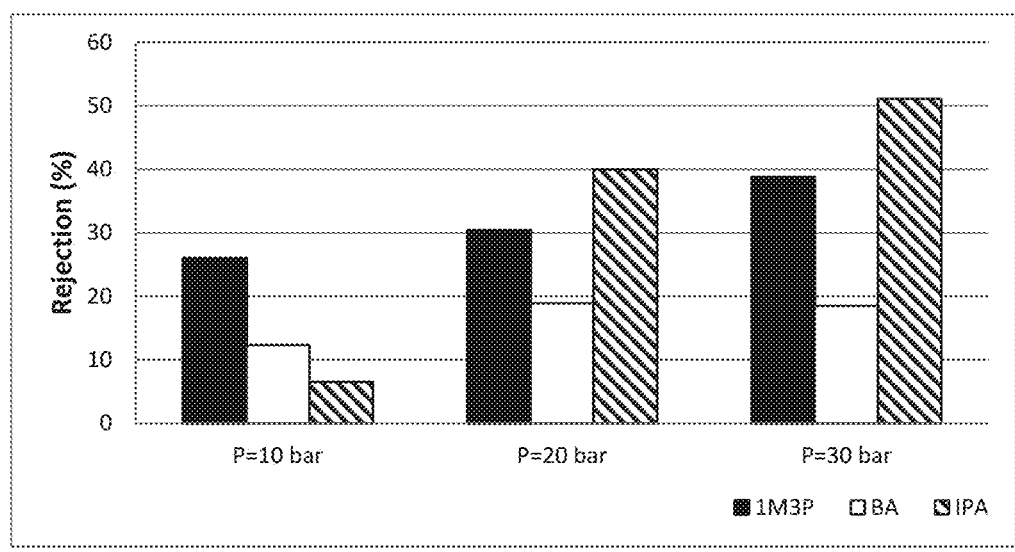

The results are shown in FIG. 10 (and in Table 3B). From this figure, it can be seen that several of the membranes are able to retain more than 80% of HMW PEG-A and/or PEG-C. However, due to the low MW of IPA, IPA will not be retained by these membranes but, to the contrary, easily pass through.

Indeed, from the results in FIG. 10 and in Table 3B it can be seen that, with the exception of Puramem membranes, all the polymeric membrane retained more than 80% of the tested Jeffamines by size exclusion mechanism. In contrast, the transport of the small BA and MPPA solutes across polymeric nanofiltration membranes is an extremely complex process and is dependent on a combination of steric, Donnan, dielectric and transport effects (cf. Mohammad, A. W. et al. in Desalination 356, 226-254 (2015)). For further off line investigations on substrate/product separation, in addition to the Desal DK-GE membrane (DESAL® DK NF (Lenntech)), which showed the highest rejection for AD 6, DuraMem® 200 (Evonic) was also chosen (DuraMem® 200 and DESAL® DK being two commercial, pH-stable nanofiltration (NF) membranes). A relatively high flux was observed, also when using this organic solvent nanofiltration (OSN) membrane.

TABLE 3B

Membrane rejections toward AD 3 (400 g/mol) and AD 6 (600 g/mol). Synthetic solutions containing 250 mM AD 3 or AD 6, 0.1 mM PLP, 100 mM CHES buffer, pH 9.5 were used.

| | Rejection % | |
|---|---|---|
| Membrane | AD 3 (400 g/mol) | AD 6 (600 g/mol) |
| Synder NFX | 85.9 | 85.9 |
| Synder NFW | 82.3 | 85.1 |
| Duramem200 | 79.7 | 85.7 |
| SolSep-10206 | <30 | 83.8 |
| GE KH Duracid | n.a | 62.2 |
| Desal-DK-GE | 85.0 | 87.5 |
| Alfalaval NF99 | n.a | 83.2 |
| Dow NF90 | n.a | 83.0 |
| Puramem Flux | <30 | n.a |
| Puramem Performance | <30 | n.a |
| PuraMem selective | <30 | n.a | n.a, not tested due to very low fluxes

Example 5: Distribution of Components

The distribution of ketosubstrate (benzylacetone, BA), HMW or LMW amino donor (AD) (either HMW PEG-A, HMW PEG-C, or LMW IPA) and chiral product (1-methyl-3-phenylpropylamine, 1 M3P (or MPPA)) is investigated, performing offline membrane extraction experiments (off line nanofiltration with model solutions). Thereto, (model) aqueous solutions having the composition expected after 24 h of performing a transamination reaction were prepared and subsequently separated using a membrane unit according to aspects of the disclosure. Either DuraMem® 200 or DESAL® DK NF were used as commercially available nanofiltration (NF) membranes in the membrane unit.

More particularly, 5 mM BA (benzylacetone) ketosubstrate, 5 mM 1 M3P (1-methyl-3-phenylpropylamine) amine product, 250 mM amino donor (either HMW (AD 3 or AD 6) or LMW AD) and 0.1 mM pyridoxal phosphate (PLP) were dissolved in 100 mM CHES buffer at pH 9.5. A high pressure stainless steel cross-flow membrane (filtration) unit, specifically designed to work with both aqueous and organic solvent based streams was used. The test unit basically consisted of a feed vessel (capacity of approximately 1 L), a gear pump for circulation, and a rectangular membrane housing. The permeate passing through the membrane was collected in a recipient placed on a balance. Membranes were tested at room temperature, at a pressure of 10, 20 and 30 bar. Samples of permeate and retentate (the latter being the solution rejected by the membrane, i.e. not passing through the membrane) were taken at steady-state conditions (stable flux), and membrane rejections were calculated as follows:

$$R\ (\%) = \left(1 - \frac{C_p}{C_r}\right) * 100$$

where $C_p$ and $C_r$ denote the measured concentrations in the permeate and retentate, respectively.

Membrane tests were performed at room temperature, and three pressures, viz. 10, 20 and 30 bar, were applied. Permeate and retentate samples were taken at steady-state conditions (stable flux), and rejections were calculated.

The results are summarized in Tables 4 to 8, and shown in FIGS. 11 to 15.

TABLE 4

Rejection (in %) of reaction components using HMW PEG-A and DESAL ® DK NF membrane

|       | p = 10 bar | p = 20 bar | p = 30 bar |
|-------|------------|------------|------------|
| 1M3P  | −7.18      | −59.16     | −21.53     |
| BA    | 48.41      | 37.29      | 42.50      |
| PEG-A | 73.90      | 94.50      | 97.14      |

TABLE 5

Rejection (in %) of reaction components using HMW PEG-A and DuraMem ® 200 NF membrane

|       | p = 10 bar | p = 20 bar | p = 30 bar |
|-------|------------|------------|------------|
| 1M3P  | 8.12       | 1.29       | 19.15      |
| BA    | 39.75      | 37.38      | 41.56      |
| PEG-A |            | 79.76      | 86.97      |

TABLE 6

Rejection (in %) of reaction components using HMW PEG-C and DESAL ® DK NF membrane

|       | p = 10 bar | p = 20 bar | p = 30 bar |
|-------|------------|------------|------------|
| 1M3P  | 26.69      | −120.91    | −98.31     |
| BA    | 66.13      | 40.77      | 42.29      |
| PEG-C | 67.57      | 87.76      | 94.01      |

TABLE 7

Rejection (in %) of reaction components using HMW PEG-C and DuraMem ® 200 NF membrane

|       | p = 10 bar | p = 20 bar | p = 30 bar |
|-------|------------|------------|------------|
| 1M3P  | 5.36       | −28.05     | −27.18     |
| BA    | 43.00      | 37.88      | 41.72      |
| PEG-C | 53.92      | 76.36      | 82.15      |

TABLE 8

Rejection (in %) of reaction components using LMW IPA and DuraMem ® 200 NF membrane

|       | p = 10 bar | p = 20 bar | p = 30 bar |
|-------|------------|------------|------------|
| 1M3P  | 26.00      | 30.38      | 38.74      |
| BA    | 12.32      | 18.92      | 18.46      |
| IPA   | 6.52       | 39.94      | 51.08      |

As expected, based on their HMW, amino donors PEG-A and PEG-C, were well retained by the NF membranes (cf. Tables 4 to 7). The highest amount of HMW AD was rejected by the membrane when operating at a pressure of 30 bar.

From Table 8, it can be seen that LMW IPA was also retained by the DuraMem® 200 NF membrane, however, not to the same extent as the HMW amino donors when operating at similar pressure.

Moreover, it can be seen that retention of the ketosubstrate and extraction of the amine product is beneficial when using solutions containing PEGs instead of IPA. Indeed, around 40% of BA substrate was retained when using PEG solutions (cf. Tables 4 to 7), while maximum 18% BA substrate was retained when using the IPA solution (cf. Table 8). Furthermore, it can be seen that the amine product is preferentially extracted, even over-concentrated, when using PEG solutions instead of IPA.

Indeed, the off-line tests revealed (cf. FIG. 11-15) that BA was partially retained by both membranes. On the contrary, MPPA solute was transported across the membrane faster than the solute hence achieving negative rejections. Surprisingly, Desal DK showed higher BA/MPPA selectivity compared to DuraMem® 200. This result suggests that there is a correlation between the hydrophilicity of the membrane and its capacity to permeate the product amine while retaining the substrate. As expected, the retention (rejection) for HMW amines was >80% for both membranes. Overall, the membrane investigation indicates that NF can be used for ISPR of the (model) chiral product. By using a stable and highly selective membrane, thermodynamic equilibrium as well as product inhibition issues can be easily addressed without any consistent contamination of the product stream.

Example 6: Intermittent On/Off Line NF Coupled with Enzymatic Reaction

Having proven the effectiveness of both reaction and separation operations, process implementation was further investigated. Reaction was scaled up from one to 500 mL scale (data not shown).

Reaction was performed in 600 mL volume containing 2 mg/mL of TA_v2 powder, 250 mM AD 6, 10 mM BA substrate (dissolved in DMSO) and 0.1 mM PLP in 100 mM CHES buffer, pH 9.5. The final DSMO concentration was 5% (v/v). After 16 h of reaction, 550 mL of reaction mixture was transferred into the membrane unit and 2 intermittent nanofiltration tests were performed. The remaining 50 mL of reaction mixture was used as control without filtration. After the first nanofiltration (6 h duration, DESAL® DK, 20 bar), the collected permeate and the retentate were mixed, and 5 mM of additional BA substrate were added. Additional substrate was added also to the control condition. After 16 h of reaction, the second nanofiltration was performed (5 h duration, DuraMem® 200, 20 bar). Reaction permeate and retentate samples were taken after distinct time periods and prepared for quantitative analysis. Table 9 summarizes each step of the test.

TABLE 9

Summary of the intermittent On/Off line NF test.

| Step | Step | | Time (h) | Volume (mL) |
|---|---|---|---|---|
| | First reaction and separation step | | | |
| 1 | Reaction_1 | 10 mM BA; 250 mM PEG-C; 0.1 mM PLP in CHES buffer, pH 9.5. 30° C. | ~16 | 600 |
| | Separation_1 (NF-1) | Desal DK-GE; P = 20 bar | ~6 | 550 |
| 2 | Control-reaction_1 | 10 mM BA; 250 mM PEG-C; 0.1 mM PLP in CHES buffer, pH 9.5. 30° C. | ~6 | 50 |
| | | Second reaction and separation step | | |
| 3 | Reaction 2 | Permeate and retentate were mixed; 5 mM BA was added | ~16 | 550 + 50 |
| | Separation_2 (NF-2) | DuraMem ® 200; P = 20 bar | ~5 | 550 |
| 4 | Control-reaction_2 | 15 mM BA; 250 mM PEG-C; 0.1 mM PLP in CHES buffer, pH 9.5. 30° C. | ~5 | 50 |

Figure 16:
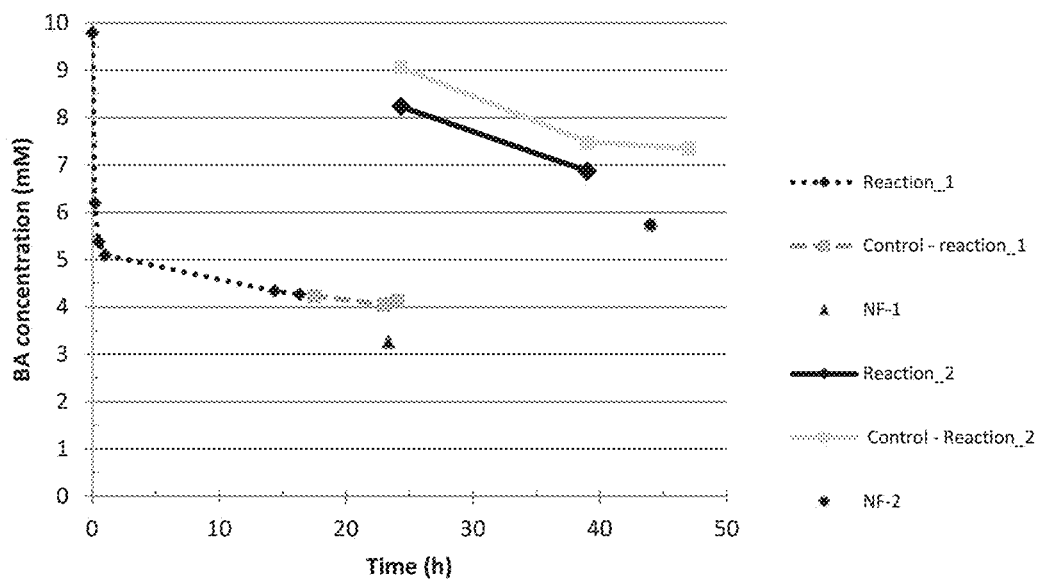
FIG. 16 shows intermittent on/off line nanofiltration coupled with enzymatic reaction: BA substrate consumption in function of time.

FIG. 16 shows intermittent on/off line nanofiltration coupled with enzymatic reaction: BA substrate consumption in function of time Initial amount of BA substrate and AD 6 were 10 and 250 mM, respectively; the first nanofiltration was run after 16 h reaction (Desal-DK membrane, 20 bar). Addition of BA (5 mM) was made to the enzymatic tank E-1 after 24 h reaction. The second nanofiltration was run after 39 h reaction (DuraMem® 200 membrane, 20 bar).

As also summarized in Table 9, the first asymmetric amination coupled with NF separations was conducted intermittently employing the solvent stable TA-v2 enzyme. In accordance with stability experiments, ~55% of BA was converted in 16 h (FIG. 16, Reaction_1). Thermodynamic equilibrium was almost reached since only 2% of BA substrate was further converted in the following 6 h (FIG. 16, Control-reaction_1). In contrast, 6 h of NF enhanced additional 10% substrate conversion hence showing the benefit of in situ product removal for thermodynamic equilibrium shifting (FIG. 16, NF-1). After 5 mM substrate addition, additional ~17% BA was converted in 16 h in both NF reaction mixture and control (FIG. 16, Reaction_2 and Control-Reaction_2). Although reaction rate decreased, TA-v2 enzyme was still active in both control and NF system hence demonstrating that this enzyme, in presence of the HMW amine donor (AD 6) can withstand the mechanical stress of the NF unit (high pressure and high stirring rate).

Figure 17:
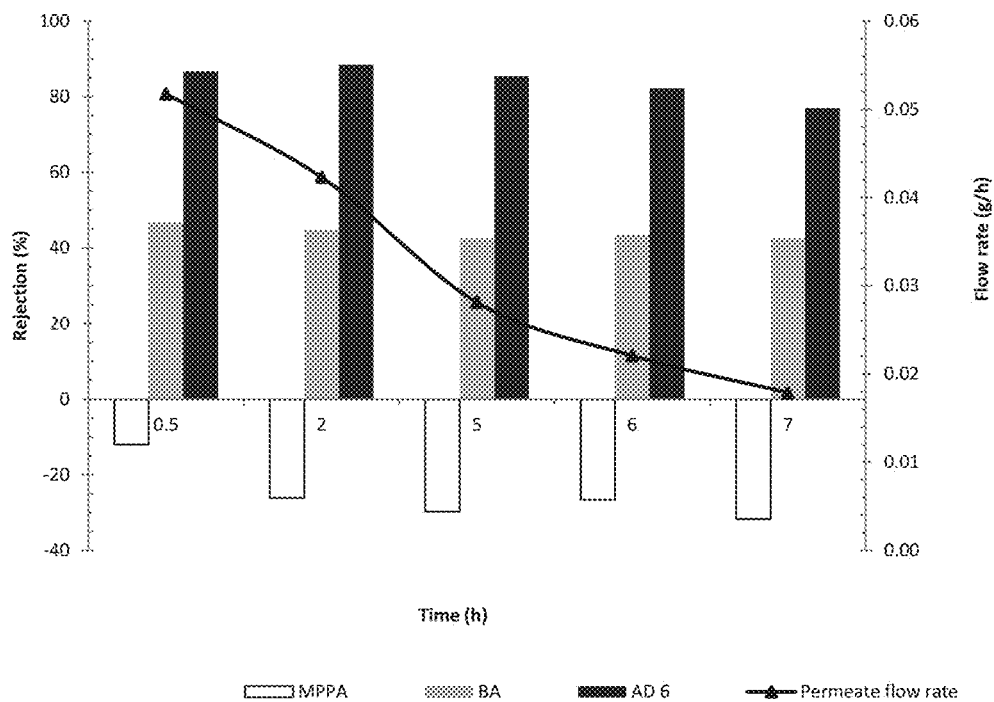
FIG. 17 shows NF-1 intermittent on/off test: rejections (bars) and total permeate flow rate in function of time (0.5 h, 2 h, 5 h, 6 h, 7 h) when using Desal DK-GE membrane.
Figure 18:
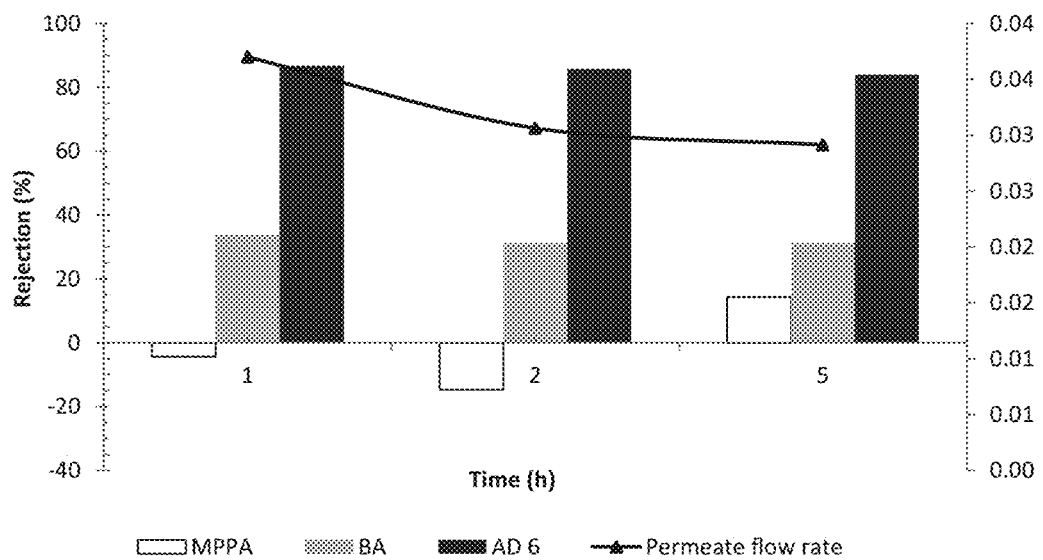
FIG. 18 shows NF-2 intermittent on/off test: rejections (bars) and total permeate flow rate in function of time (1 h, 4 h, 5 h) when using DuraMem® 200 membrane.

The selective product removal using DuraMem® 200 boosted the equilibrium on the product enhancing additional 15% product formation (FIG. 16, NF-2). In accordance with membrane screening and off line tests, more than 80% PEG-C was retained when using both membranes (FIG. 17 and FIG. 18). Desal-DK selectively over-concentrated the MPPA (1-methyl-3-phenyl propylamine) product, however, together with the product, ~58% of unreacted substrate was lost in the permeate stream. Permeate flux decline, observed when using Desal DK could be connected to interaction of the membrane with MPPA and BA solutes (cf. Van der Bruggen et al. in Environ. Sci. Technol. 35, 17, 3535-3540). More likely, flux decline was due to shrinking of the membrane matrix (cf. Yang, X. J. et al. in J. Membr. Sci., 190 (2001) 45-55). Desal DK is a nanofiltration membrane designed for aqueous systems therefore it probably lost its structural integrity upon prolonged exposure to MPPA, HMW amines and BA solutes. Especially the co-solvent DMSO, employed for enhancing substrate solubility, could have affected membrane performances. The visual observations of the tested membranes confirmed this assumption. In contrast, no changes to the active surface of DuraMem® 200 membrane were visually observed. On the contrary, this organic solvent nanofiltration (OSN) membrane resulted to be stable even when exposed to higher substrate and DMSO co-solvent concentrations.

Figure 19:
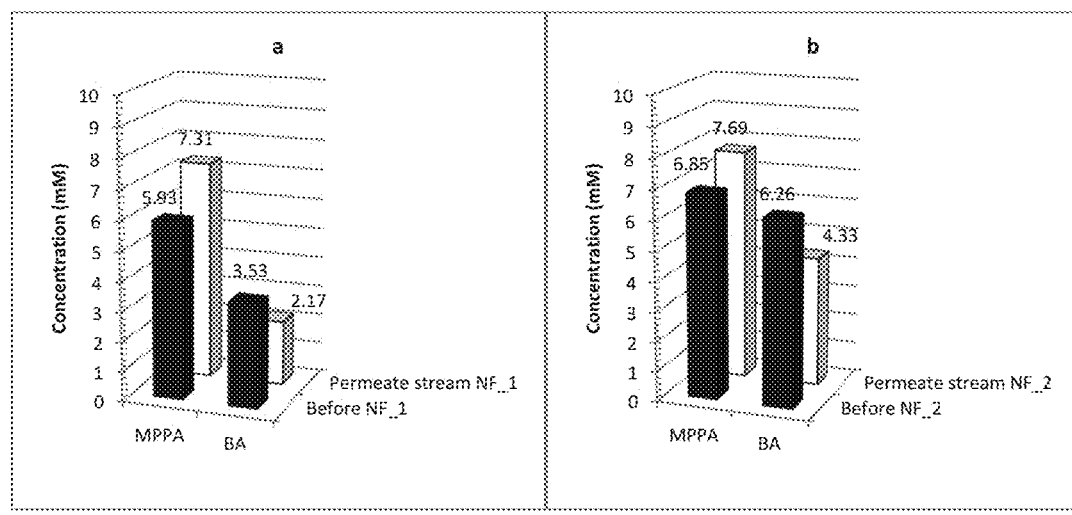
FIG. 19 shows concentration of MPPA product and BA substrate before (black bars) and after (white bars) nanofiltration with Desal DK (FIG. 19a) and DuraMem® 200 (FIG. 19b)

In addition to amine donor retention and thermodynamic equilibrium shifting, a highly selective membrane would enhance concentration of the product in a less diluted water stream. Due to the selective removal of MPPA product, faster than the transport of the solvent (buffer) across Desal-DK membrane, MPPA concentration raised from 5.9 mM to 7.3 mM while the partial retention of BA substrate reduced product stream contamination (FIG. 19a). Even if less selective, DuraMem® 200 enhanced thermodynamic equilibrium shifting and MPPA concentration in a less diluted stream as well (FIG. 19b).

Example 7: On Line Nanofiltration Coupled with Enzymatic Reaction

Figure 20:
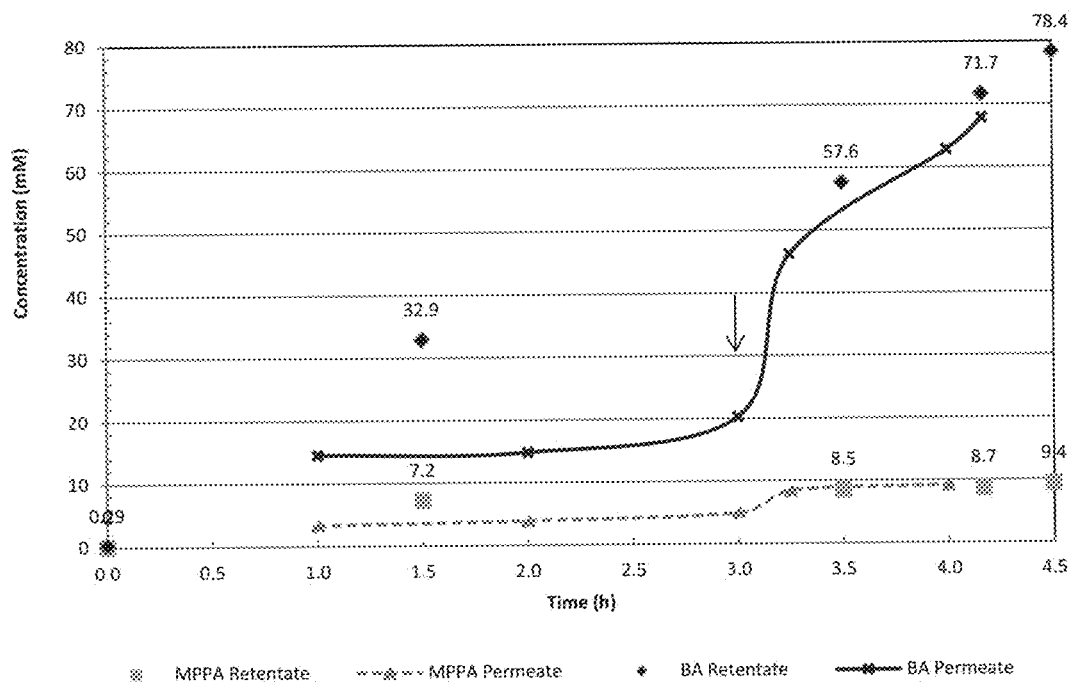
FIG. 20 shows on line nanofiltration (Desal-DK membrane) coupled with the enzymatic reaction.

High reaction rate combined with relatively low permeate fluxes and selective product removal suggested on line NF with continuous substrate feeding through P-1 diafiltration pump (FIG. 3) as a smart feeding strategy for further process optimization. Diafiltration depends on the permeate flow rate since it occurs at the same rate of permeation. Therefore, reaction and permeation rates are to be matched. When solution of high concentrated substrate (BA 200 mM in DMSO) was subjected to diafiltration, BA was accumulating in the enzymatic tank 6 (FIG. 20). Moreover, the best performing Desal-DK membrane resulted to be incompatible with high quantities of BA, MPPA and DMSO, while the solvent stable DuraMem® 200 showed lower product selectivity at high substrate concentrations (FIG. 21).

FIG. 20 shows on line nanofiltration (Desal-DK membrane) coupled with the enzymatic reaction. Permeate flux was very low, therefore BA was manually diafiltrated (40 mM). After 1.5 h, 18% BA was converted. After 3 h experiment, the flux suddenly increased; 200 mM BA feed solution was automatically diafiltrated at the same rate of permeation, therefore BA retentate concentration increased (black dots) in the enzymatic tank (cf. FIG. 3, enzymatic tank (6)). BA retention drastically decreased when the flux increased (black line); MPPA concentration poorly increased with BA addition (light grey dots).

Figure 21:
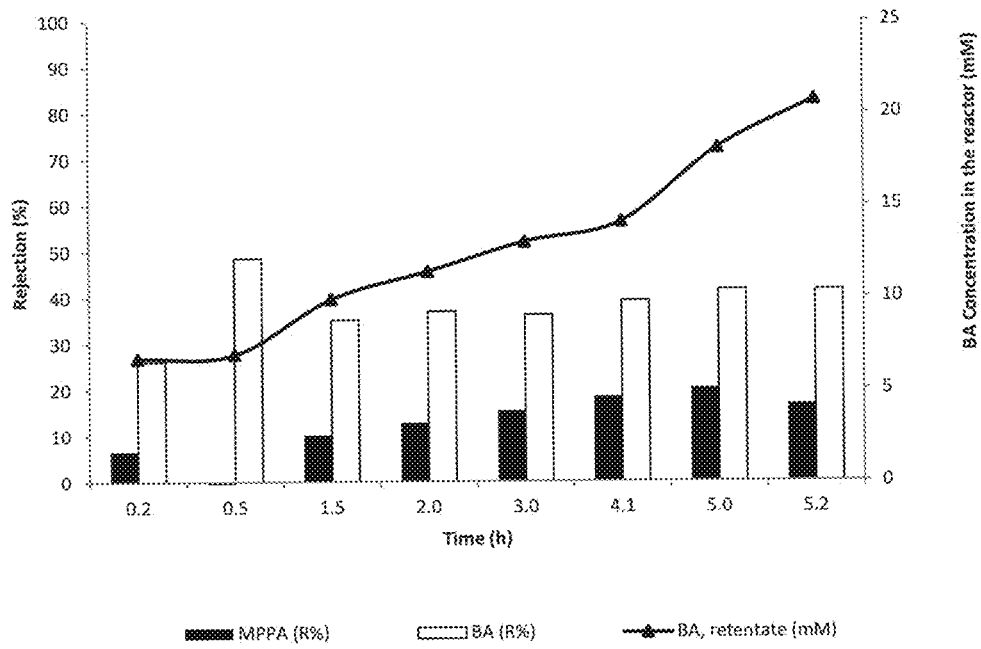
FIG. 21 shows on line nanofiltration (DuraMem® 200 membrane) coupled with the enzymatic reaction.

FIG. 21 shows on line nanofiltration (DuraMem® 200 membrane) coupled with the enzymatic reaction. The selective product removal (black bars) decreased with the increase of substrate concentration (black line). Since permeation and reaction rates did not match, BA accumulated in the enzymatic tank (cf. FIG. 3, enzymatic tank (6)).

The above examples 1-7 demonstrate that HMW donors can successfully be used in transamination processes, i.e. for synthesis and membrane assisted in situ product recovery of chiral amines.

The invention claimed is:

1. A method for producing a chiral amine, the method comprising:
    forming a chiral amine and a co-product in a first solution by performing a transamination reaction of a prochiral amino acceptor and an amino donor in the first solution in the presence of a transaminase;
    wherein the amino donor is a high molecular weight (HMW) amino donor, and wherein (a) a molecular weight of the high molecular weight amino donor is at least 200 g/mol, or (b) the amino donor is affixed on an inert support, a total molecular weight of the amino donor and the inert support being at least 200 g/mol; and
    separating the chiral amine from the first solution using a porous membrane having a molecular weight cut-off, such that the porous membrane is configured to retain the unreacted amino donor in the first solution while allowing the chiral amine to permeate through the porous membrane.

2. The method of claim 1, wherein the molecular weight of the high molecular weight amino donor, or the total molecular weight of the amino donor and the inert support, is at least 300 g/mol.

3. The method of claim 1, wherein the amino donor comprises at least one amino group.

4. The method of claim 1, wherein the amino donor is an amine having a general formula

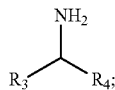

and
    wherein each of $R_3$ and $R_4$ is independently selected from the group consisting of: hydrogen, linear or branched saturated alkyl group, linear or branched unsaturated alkyl group, cycloalkyl group, heterocyclyl group, heterocyclylalkyl group, aryl group, aralkyl group, heteroaryl group, acyl group, hydroxyl group, linear or branched saturated alcohol, linear or branched unsaturated alcohol, alkoxy group, aryloxy group, amino group, alkylamino group, cycloalkylamino group, arylamino group, acyloxy group, acylamino group, cyano group, nitrile, carboxyl group, thio group, thiol group, aminocarbonyl group, carbamoyl group, arlyoxycarbonyl group, phenoxycarbonyl group, alkoxycarbonyl group, haloalkyl group, and halogen.

5. The method of claim 1, wherein the HMW amino donor is selected from the group consisting of: poly(ethylene glycol) bis (3-aminopropyl), 1,4-bis(3-aminopropyl)piperazine, poly(propylene glycol) bis(2-aminopropyl ether), O-(2-Aminopropyl)-O'-(2-methoxyethyl)polypropylene glycol, O,O'-Bis(2-aminopropyl) polypropylene glycol-block-polyethylene glycol-block-polypropylene glycol, and 1,2-bis(3-aminopropylamino)ethane.

6. The method of claim 1, wherein the prochiral amino acceptor is a ketone substrate having a general formula

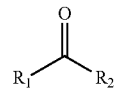

wherein the substituents $R_1$ and $R_2$ are different from each other; and
    wherein each of $R_1$ and $R_2$ is independently selected from the group consisting of: hydrogen, linear or branched saturated alkyl group, linear or branched unsaturated alkyl group, cycloalkyl group, heterocyclyl group, heterocyclylalkyl group, aryl group, aralkyl group, heteroaryl group, acyl group, hydroxyl group, linear or branched saturated alcohol, linear or branched unsaturated alcohol, alkoxy group, aryloxy group, amino group, alkylamino group, cycloalkylamino group, arylamino group, acyloxy group, acylamino group, cyano group, nitrile, carboxyl group, thio group, thiol group, aminocarbonyl group, carbamoyl group, arlyoxycarbonyl group, phenoxycarbonyl group, alkoxycarbonyl group, haloalkyl group, and halogen.

7. The method of claim 1, wherein the amino acceptor is a ketone substrate selected from the group consisting of: acetophenone, ortho-bromoacetophenone, benzylacetone, and 2-bromo-4-acetylacetanilide.

8. The method of claim 1, wherein the porous membrane is a nanofiltration membrane.

9. The method of claim 1, wherein the porous membrane has a molecular weight cut-off (MWCO) for each of the amino donor, the transaminase, and the co-product of at least 200 g/mol.

10. The method of claim 1, wherein the transaminase is 3HMU from *Ruegeria pomeroyi*, or 3FCR from Ruegeria sp. TM1040.

11. The method of claim 1, wherein the inert support is a polystyrene support.

12. The method of claim 1, wherein
    the prochiral amino acceptor is a ketone substrate selected from the group consisting of: acetophenone, ortho-bromoacetophenone, benzylacetone, and 2-bromo-4-acetylacetanilide;

the amino donor is selected from the group consisting of: (highly flexible) poly(ethylene glycol) bis (3-aminopropyl), 1,4-Bis(3-aminopropyl)piperazine, poly(propylene glycol) bis(2-aminopropyl ether), O-(2-Aminopropyl)-O'-(2-methoxyethyl)polypropylene glycol, O,O'-bis(2-aminopropyl) polypropylene glycol-block-polyethylene glycol-block-polypropylene glycol, and 1,2-bis(3-aminopropylamino)ethane; and the transaminase is 3HMU from *Ruegeria pomeroyi* or 3FCR from Ruegeria sp. TM1040.

13. The method of claim 1, wherein the prochiral amino acceptor is a ketone substrate selected from the group consisting of: acetophenone, ortho-bromoacetophenone, benzylacetone, and 2-bromo-4-acetylacetanilide;

the amino donor is poly(propylene glycol) bis(2-aminopropyl ether); and the transaminase is 3HMU from *Ruegeria pomeroyi*.

14. The method of claim 1, wherein the prochiral amino acceptor is a ketone substrate selected from the group consisting of: acetophenone, ortho-bromoacetophenone, benzylacetone, and 2-bromo-4-acetylacetanilide;

the amino donor is O,O'-bis(2-aminopropyl) polypropylene glycol-block-polyethylene glycol-block-polypropylene glycol; and the transaminase is 3HMU from *Ruegeria pomeroyi*.

15. A method for producing a chiral amine, the method comprising:

forming a chiral amine and a co-product in a first solution by performing a transamination reaction of a prochiral amino acceptor and an amino donor in the first solution in the presence of a transaminase;

wherein the amino donor is a high molecular weight amino donor, and wherein the high molecular weight amino donor is poly(ethylene glycol) bis (3-aminopropyl), 1,4-bis(3-aminopropyl)piperazine, poly(propylene glycol) bis(2-aminopropyl ether), O-(2-Aminopropyl)-O'-(2-methoxyethyl)polypropylene glycol, O,O'-Bis(2-aminopropyl) polypropylene glycol-block-polyethylene glycol-block-polypropylene glycol, or 1,2-bis(3-aminopropylamino)ethane; and separating the chiral amine from the first solution using a porous membrane having a molecular weight cut-off, such that the porous membrane is configured to retain the unreacted amino donor in the first solution while allowing the chiral amine to permeate through the porous membrane.

16. The method of claim 4, wherein substituents $R_3$ and $R_4$ are the same as each other.

17. The method of claim 4, wherein substituents $R_3$ and $R_4$ are the different from each other.

18. A method for producing a chiral amine, the method comprising:

forming a chiral amine and a co-product in a first solution by performing a transamination reaction of a prochiral amino acceptor and an amino donor in the first solution in the presence of a transaminase, wherein the amino donor has a molecular weight of at least 200 g/mol; and separating the chiral amine from the first solution using a porous membrane having a molecular weight cut-off, such that the porous membrane is configured to retain the unreacted amino donor in the first solution while allowing the chiral amine to permeate through the porous membrane.

19. The method of claim 1, wherein the molecular weight cut-off of the porous membrane is configured to substantially retain the transaminase and the co-product in the first solution.

20. The method of claim 1, wherein the prochiral amino acceptor is a carbonyl compound.

* * * * *